(12) United States Patent
Liu et al.

(10) Patent No.: US 11,459,298 B2
(45) Date of Patent: *Oct. 4, 2022

(54) CLASS OF DICATIONIC COMPOUNDS AS WELL AS THE PREPARATIVE METHOD AND THE USE THEREOF

(71) Applicant: WEST CHINA HOSPITAL, SICHUAN UNIVERSITY, Sichuan (CN)

(72) Inventors: Jin Liu, Sichuan (CN); Jun Yang, Sichuan (CN); Wensheng Zhang, Sichuan (CN); Bowen Ke, Sichuan (CN); Weiyi Zhang, Sichuan (CN); Cheng Zhou, Sichuan (CN); Lei Tang, Sichuan (CN)

(73) Assignee: WEST CHINA HOSPITAL, SICHUAN UNIVERSITY, Sichuan (CN)

(*) Notice: Subject to any disclaimer, the term of this patent is extended or adjusted under 35 U.S.C. 154(b) by 0 days.

This patent is subject to a terminal disclaimer.

(21) Appl. No.: 17/044,520

(22) PCT Filed: Jul. 24, 2019

(86) PCT No.: PCT/CN2019/097505
§ 371 (c)(1),
(2) Date: Mar. 25, 2021

(87) PCT Pub. No.: WO2020/020230
PCT Pub. Date: Jan. 30, 2020

(65) Prior Publication Data
US 2021/0214304 A1    Jul. 15, 2021

(30) Foreign Application Priority Data
Jul. 24, 2018    (CN) .......................... 201810820070.X

(51) Int. Cl.
| | | |
|---|---|---|
| *C07D 211/38* | (2006.01) |
| *C07D 295/15* | (2006.01) |
| *C07D 307/52* | (2006.01) |
| *C07D 333/20* | (2006.01) |
| *C07D 407/12* | (2006.01) |
| *C07D 409/12* | (2006.01) |

(52) U.S. Cl.
CPC .......... *C07D 211/38* (2013.01); *C07D 295/15* (2013.01); *C07D 307/52* (2013.01); *C07D 333/20* (2013.01); *C07D 407/12* (2013.01); *C07D 409/12* (2013.01)

(58) Field of Classification Search
None
See application file for complete search history.

(56) References Cited

FOREIGN PATENT DOCUMENTS

| | | |
|---|---|---|
| CN | 101588803 A | 11/2009 |
| CN | 103601650 A | 2/2014 |
| CN | 105315170 A | 2/2016 |
| CN | 108250143 A | 7/2018 |
| CN | 108727248 A | 11/2018 |
| JP | 2000019694 A | 1/2000 |

OTHER PUBLICATIONS

Halverstadt, I. F. et al.: "Hypotensors. 2-Ammonioalkyl 3-Ammonioalkanoate Salts", Journal of the American Chemical Society, vol. 81, Jul. 20, 1959 (Jul. 20, 1959), pp. 3618-3628, XP002337659, ISSN: 0002-7863, DOI: 20191011160037.
Miller, Ronald D.; "Is Atracurium an Ideal Neuromuscular Blocking Drug?" Anesthesia and Analgsia, vol. 61(9), pp. 721-722, Sep. 1982.
Belmont, Matthew R.; "Succinylcholine/Suxamethonium"; Current Opinion in Anaethesiology, 1995, 8, pp. 362-366.

*Primary Examiner* — Samantha L Shterengarts
(74) *Attorney, Agent, or Firm* — Novick, Kim & Lee, PLLC; Allen Xue

(57) ABSTRACT

A dication compound represented by formula (I), stereoisomers having the structure of formula (I) or a mixture of the stereoisomers, a pharmaceutically acceptable salt, a solvate, or a eutectic crystal, and a composition thereof, and use of a composition, are capable of producing neuromuscular junction retardation, formed of same with a pharmaceutically acceptable carrier in the field of preparation of a medicament for muscular flaccidity.

13 Claims, No Drawings

CLASS OF DICATIONIC COMPOUNDS AS WELL AS THE PREPARATIVE METHOD AND THE USE THEREOF

TECHNICAL FIELD

The present invention belongs to the field of drug synthesis, and specifically relates to a class of dicationic compounds as well as the preparative method and the use thereof.

BACKGROUND ART

During surgical anesthesia, neuromuscular blockers (also known as muscle relaxants) can produce muscle relaxation and are used to relax skeletal muscles during surgery and tracheal intubation. The above-mentioned muscle relaxants are classified into depolarization and non-depolarization types according to their action mechanism, and can be divided into four categories: ultra-short-acting, short-acting, medium-acting and long-acting according to their duration of action (Anesthesiology, 82(1), 33a, 1995).

Among depolarizing muscle relaxants, only succinylcholine is still used in clinical. Due to its special action mechanism, succinylcholine has serious side effects, such as elevated blood potassium, malignant hyperthermia, arrhythmia, increased intraocular pressure, and gastric tension, etc. The advantage of succinylcholine is that it has a short action time, such as it lasts for 10 minutes and has a rapid effect in the human body, and thus it is used as an ultra-short-acting muscle relaxant in clinical practice. Its feature is particularly suitable for emergency treatment, because in emergency situations, using muscle relaxants with longer acting time may cause severe brain damage and even death. At present, the depolarizing muscle relaxant succinylcholine is the most suitable muscle relaxant for emergency.

In addition to not having ultra-short-acting effects, non-depolarizing muscle relaxants are considered as safer muscle relaxants. Clinicians have been seeking for non-depolarizing muscle relaxants with ultra-short-actions (Anesthesia and Analgsia, 61(9), 721, 1982; Cueernt opinion in anaethesiology, 8, 362, 1995). However, all non-depolarizing muscle relaxants currently used in clinical do not have ultra-short-acting characteristics (meaning the muscle relaxant duration <10 min after single dose). For example, after single administration, the duration of muscle relaxation for micuronium is 15-20 min, while the action times for cisatracurium and rocuronium are 25-60 minutes, but the action time of pancuronium is longer than 60 min. CN101588803A discloses a non-depolarizing muscle relaxant, and cysteine at 200× the dose of the drug can be administrated to quickly reverse its muscle relaxant effect. Although the rapid regression of muscle relaxant is achieved, a large amount of sulfhydryl amino acids (such as semi-cystine) must be used, which will obviously increase medical procedures, and a large number of sulfhydryl amino acids will also increase uncertainty in safety, such as excessive cysteine results in tracheal spasm and vomiting. Therefore, the ultra-short-acting and non-depolarizing muscle relaxants that do not require reversal agents are more meet the clinical needs, and can reduce the economic burden of patients, increase the safety of patient, reduce operations of medical personnels, and save medical resources.

Content of the Invention

The object of the present invention is to provide a class of bicationic compounds as well as the preparative method and the use thereof.

The present invention first provides a bicationic compound of formula (I):

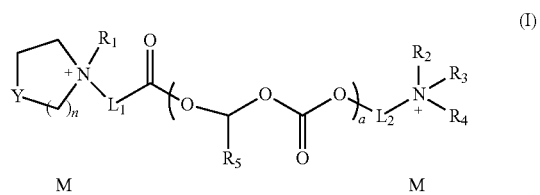

Wherein, $n=1, 2, 3$; $a=0, 1, 2$;

Y is O, substituted or unsubstituted methylene, and the substituted group is halogen and $C_1$-$C_6$ alkyl;

$L_1$ and $L_2$ are independently of each other selected from substituted or unsubstituted $C_1$-$C_8$ alkylene, wherein the substitution means that C in the alkylene is replaced by O or S and/or H is substituted by alkyl or halogen;

$R_1$, $R_2$, $R_3$, and $R_4$ are independently of each other selected from the group consisting of halogen, substituted or unsubstituted and/or saturated or unsaturated $C_1$-$C_{20}$ hydrocarbon groups, in which the substituted groups are selected from one or more halogens, alkoxys, nitros, cyanos, hydroxyls, $C_1$-$C_6$ alkyls, trifluoromethyls, $C_3$-$C_6$ heterocyclic groups, ester groups, alkoxycarbonyl groups, and the skeletons of $R_1$, $R_2$, $R_3$, and $R_4$ contain or don't contain heteroatoms;

$R_5$ is selected from H, $C_1$-$C_6$ alkyl, and $C_3$-$C_6$ cycloalkyl;

M is a pharmaceutically acceptable anion.

Further, Y is O, $CH_2$, $CHCH_3$, $CF_2$; said heteroatom is S or O. Further, $L_1$ and $L_2$ are independently of each other selected from substituted or unsubstituted $C_1$-$C_6$ alkylene, wherein the substitution means that C in the alkylene is replaced by O or S and/or H is substituted by $C_1$-$C_3$ alkyl.

Further, $R_1$, $R_2$, $R_3$, and $R_4$ are independently of each other selected from the group consisting of halogen, substituted or unsubstituted $C_1$-$C_3$ alkyl, $C_2$-$C_3$ alkenyl,

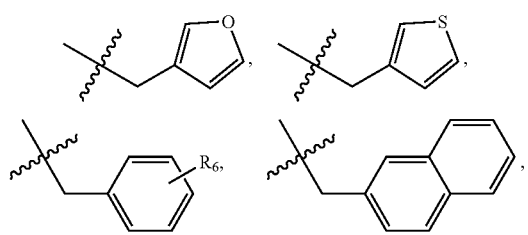

in which $R_6$ is slected from one or more H, nitros, halogens, methoxys, hydroxyls, cyanos, $C_1$-$C_3$ alkyls, phenyls, and trifluoromethyls.

Further, $n=1, 2$; $a=0, 1$.

Further, M is $Br^-$, $Cl^-$, and $R$—$SO_3^-$, and said R is a hydrocarbon group; preferably, $R$—$SO_3^-$ is selected from p-toluenesulfonate, methanesulfonate and benzenesulfonate.

Further, said halogen is F, Cl, Br, and I.

Further, when $a=1$, said compound is one of the following compounds:

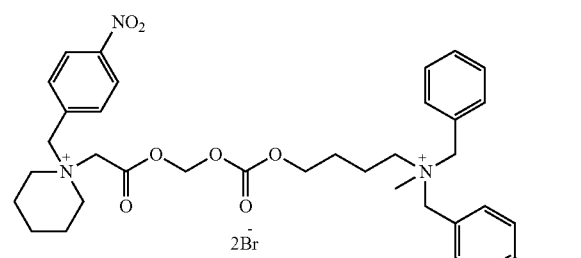
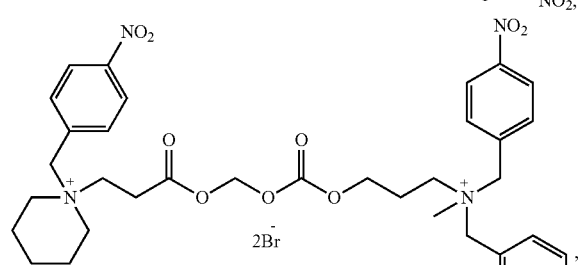
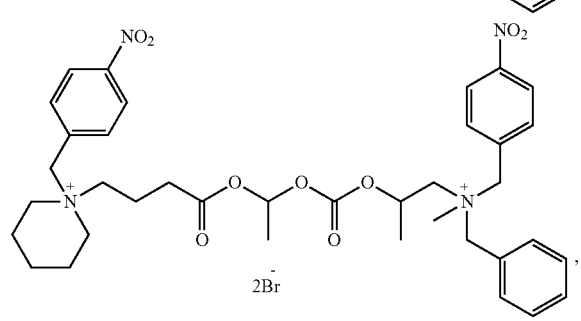
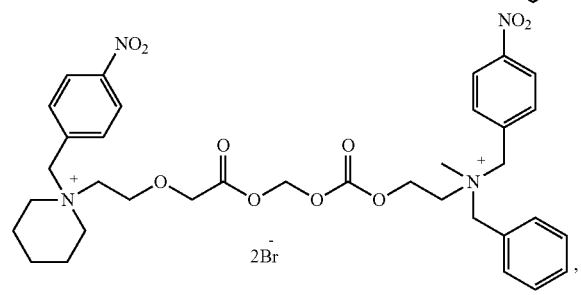
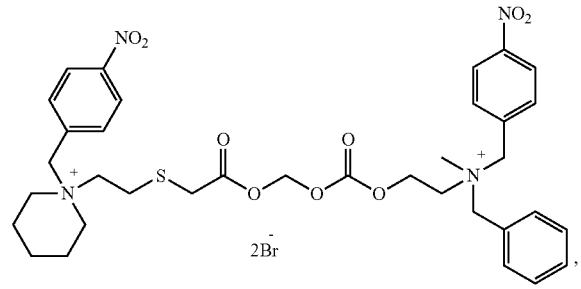
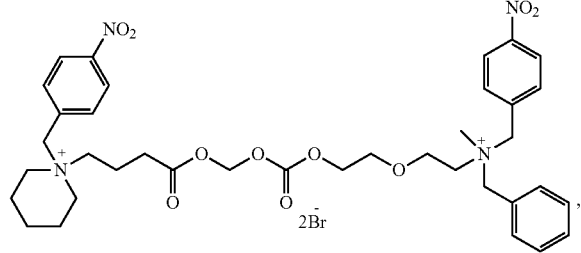
-continued
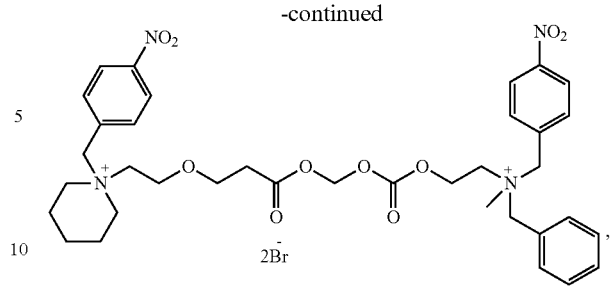
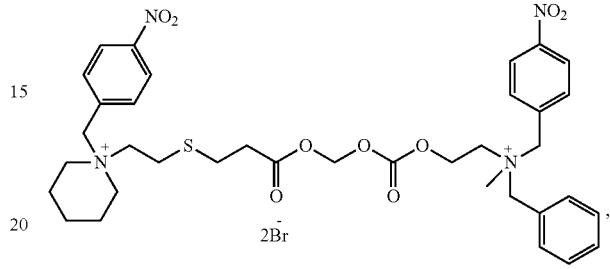
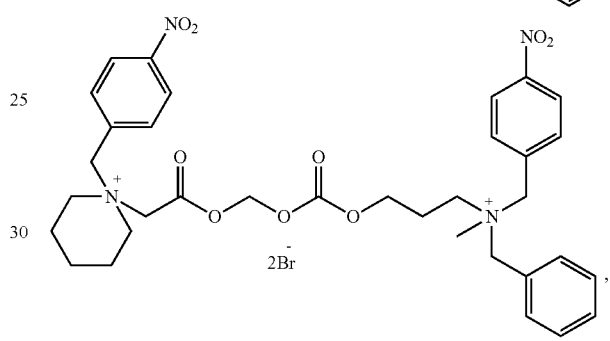
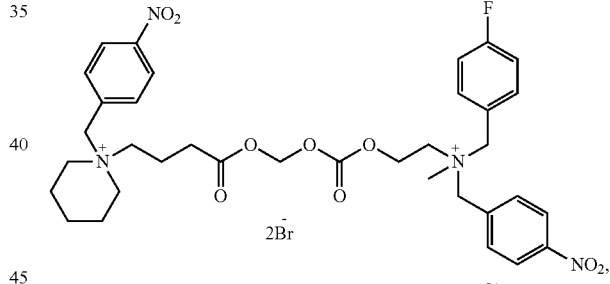
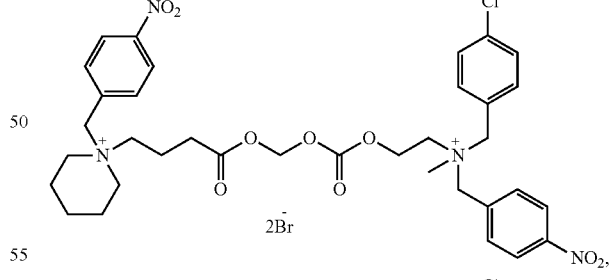
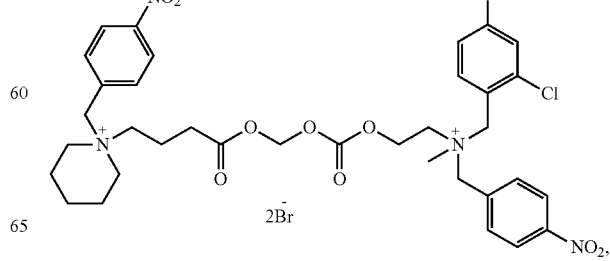

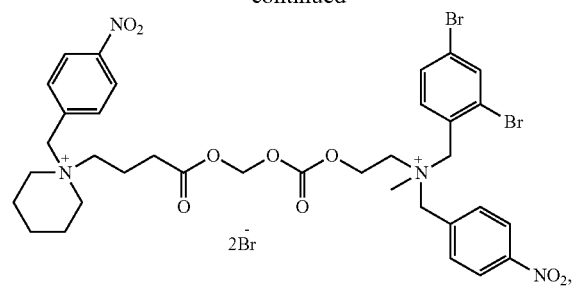
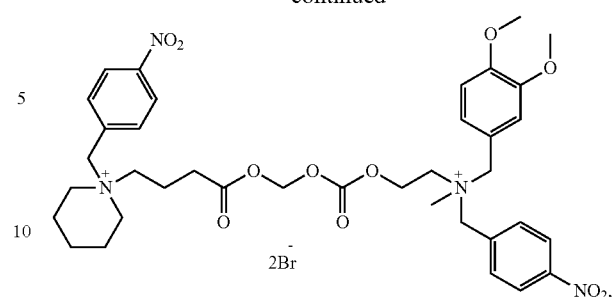
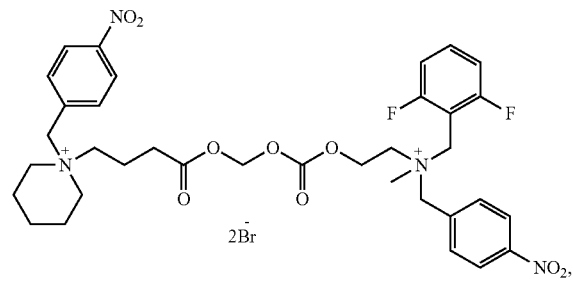
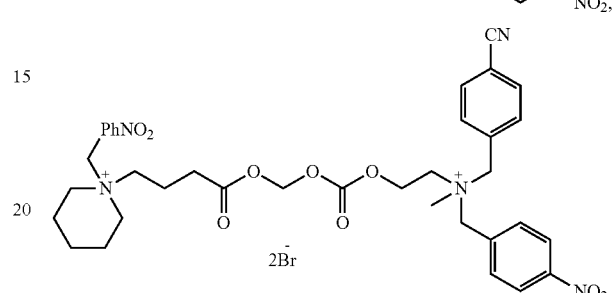
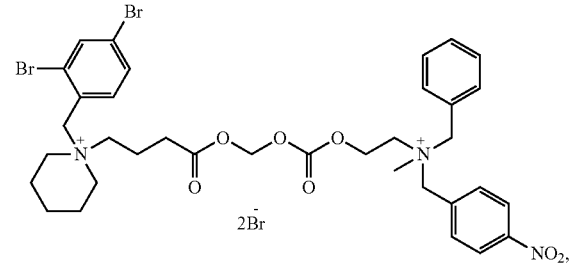
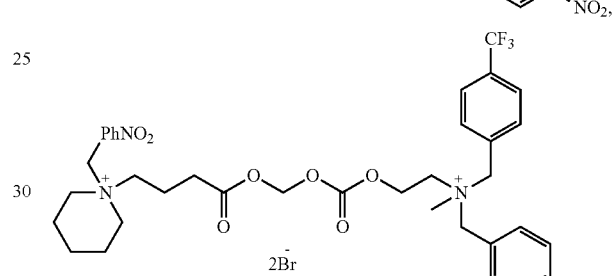
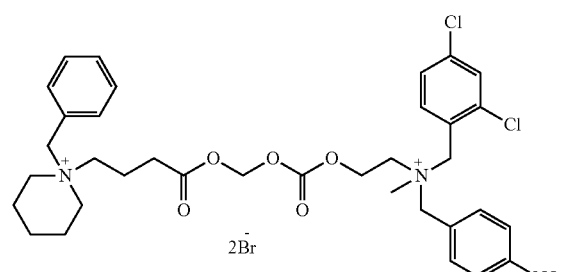
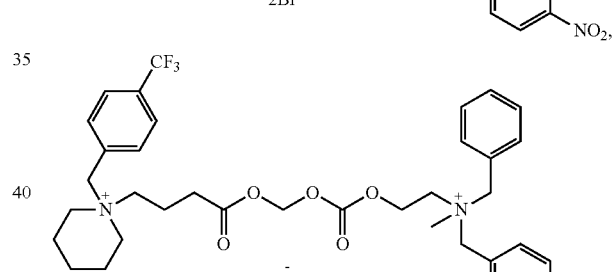
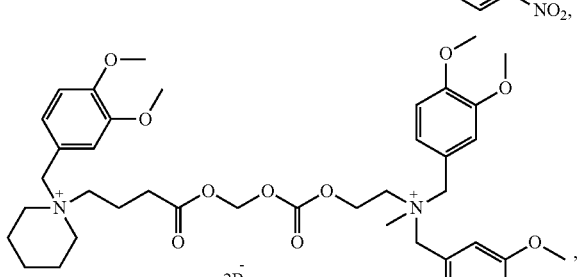
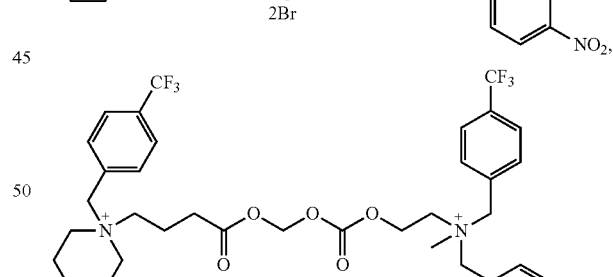
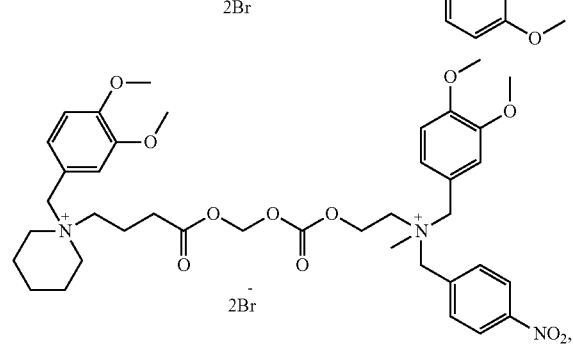
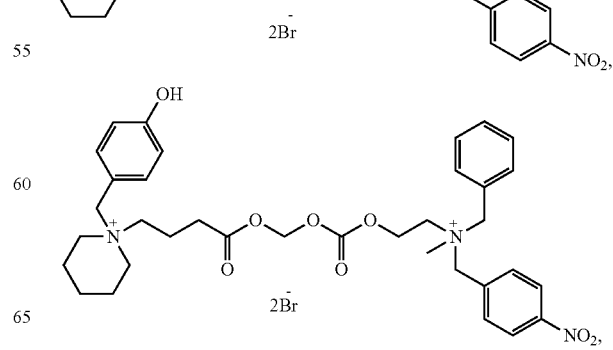

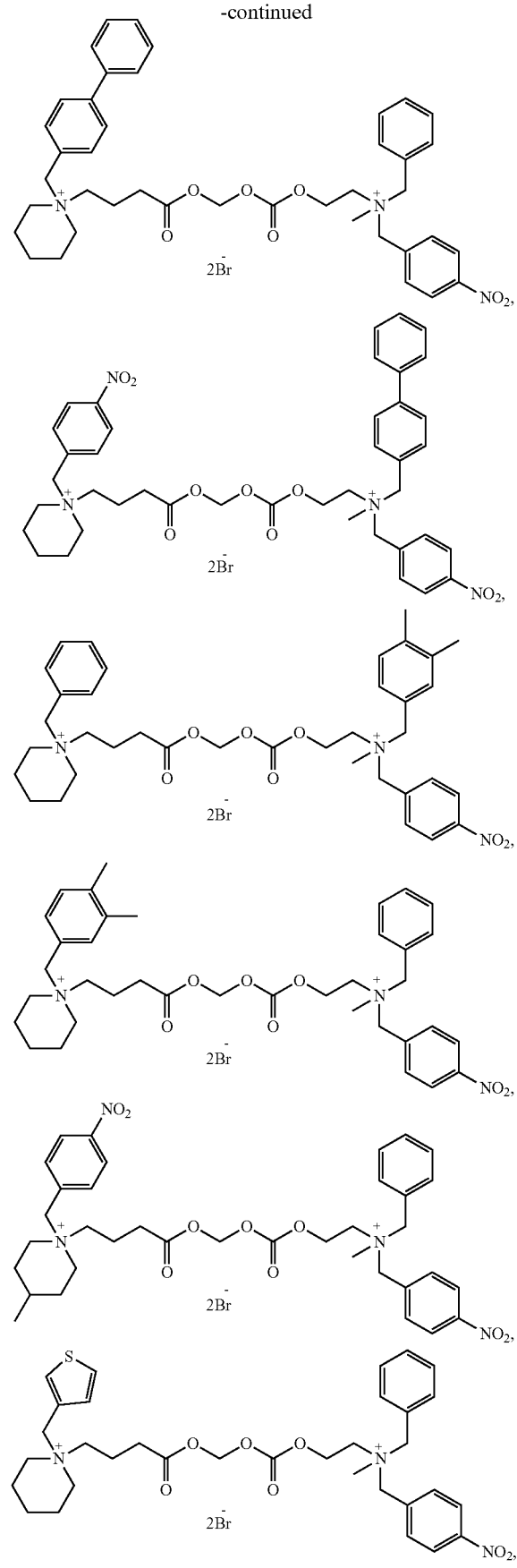
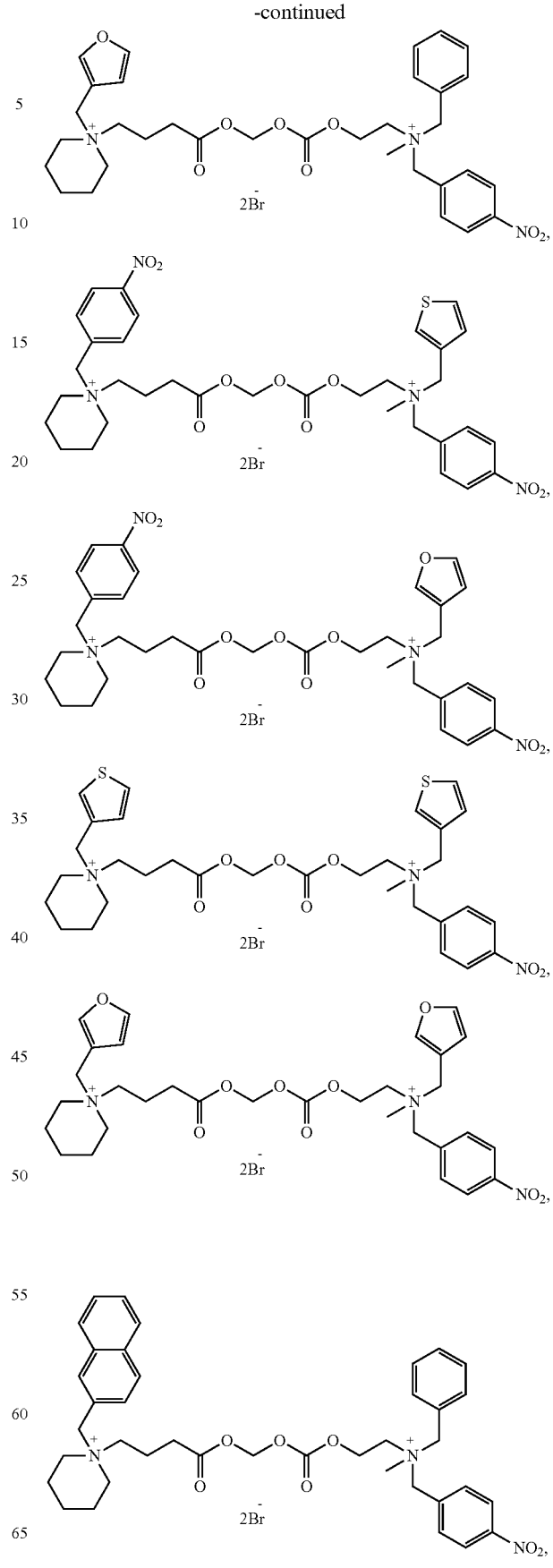

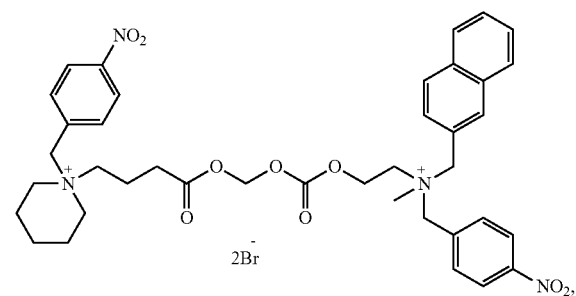
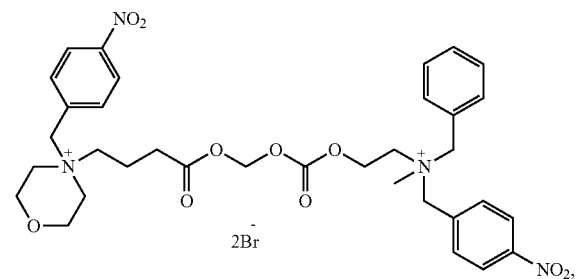
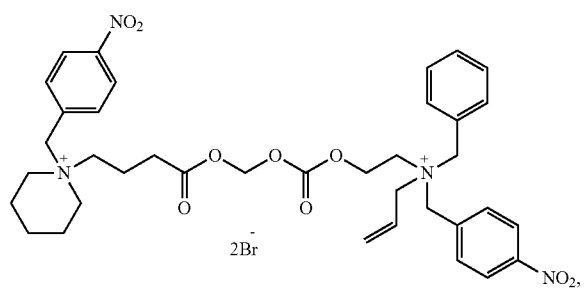
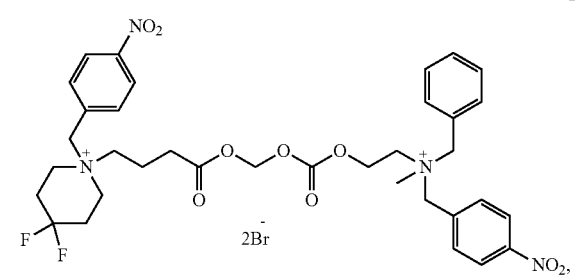
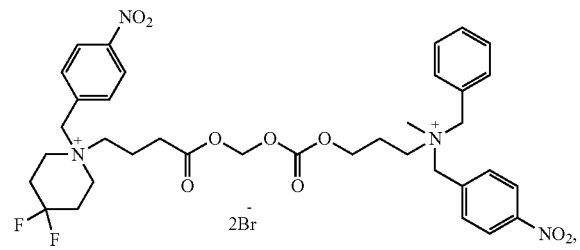
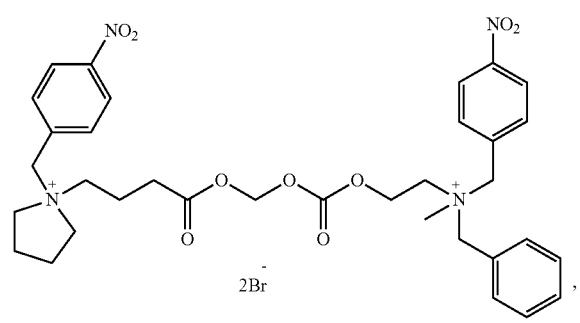
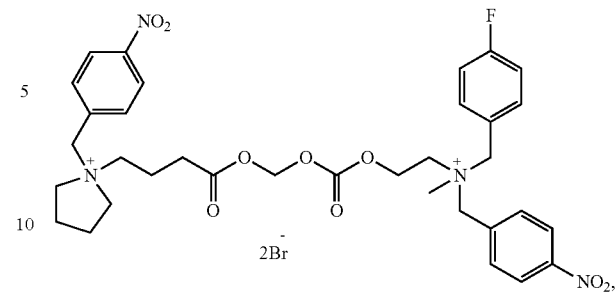
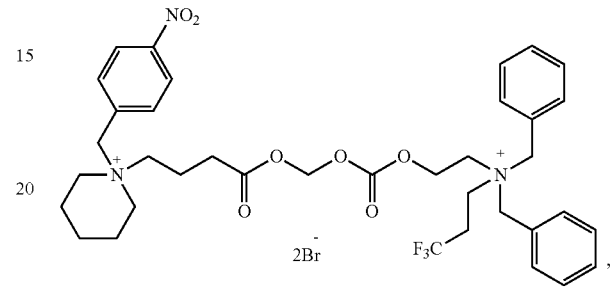
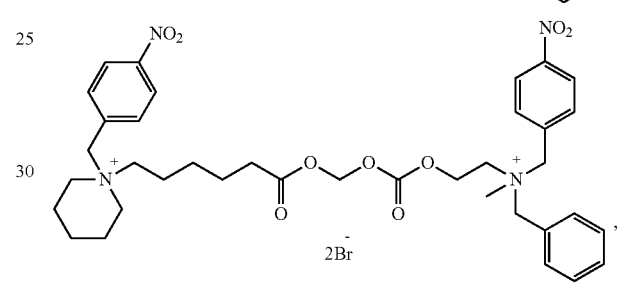
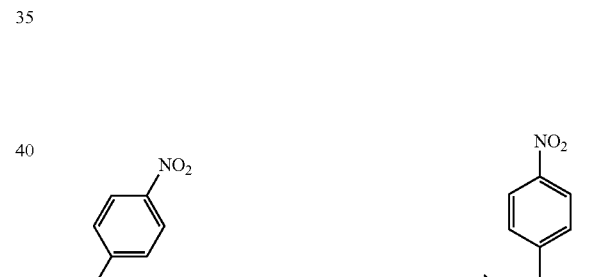
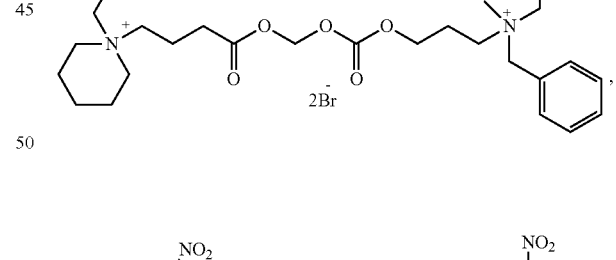
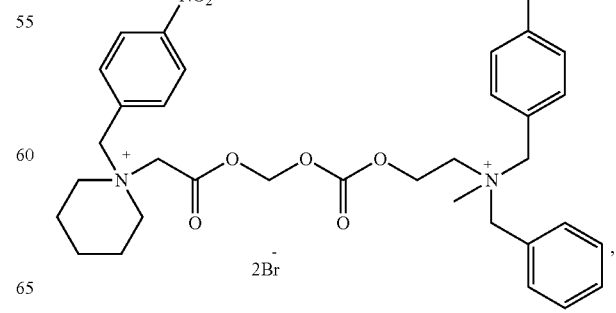

-continued

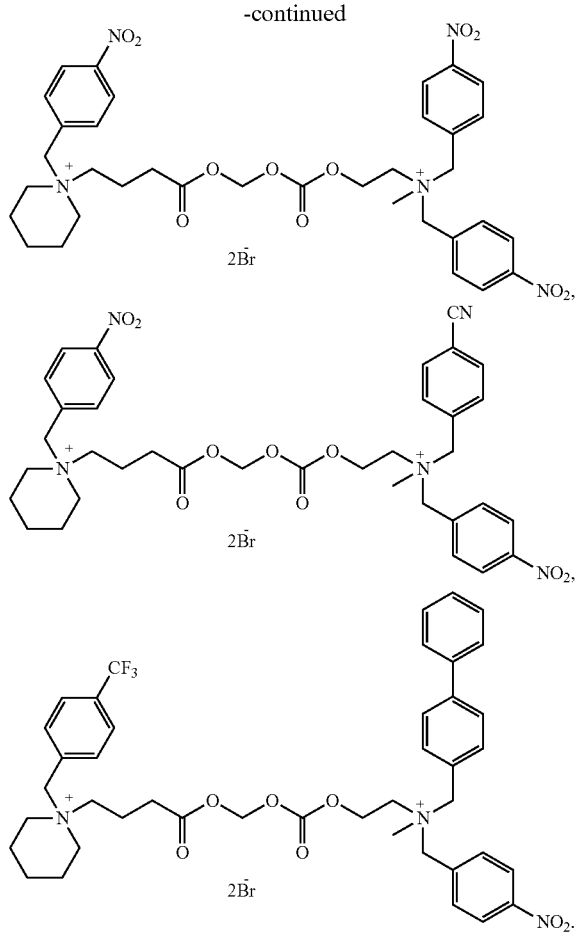

Further, when a=0, said compound is one of the following compounds:

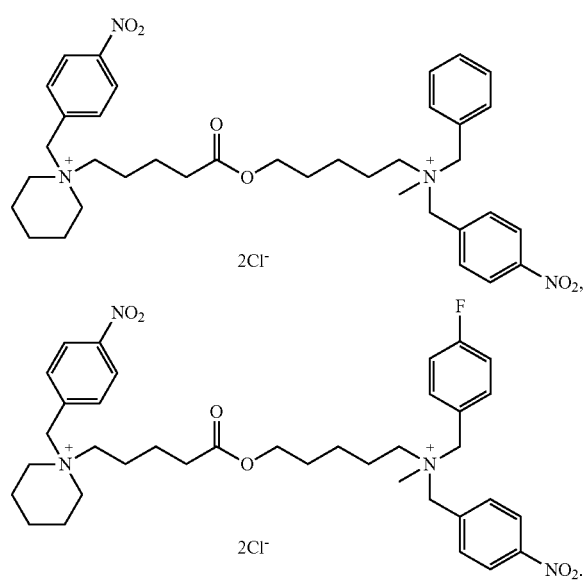

The present invention further provides the preparative method of the dicationic compound mentioned above, characterized in that the method includes the following steps:

(1) Preparation of quaternary ammonium intermediate 1
(1-i) Compound a-1 reacts with compound a-2 to prepare compound a-3;
(1-ii) Compound a-3 reacts with compound $R_1$—Br to prepare compound a-4;
(1-iii) Compound a-4 reacts with sodium hydroxide to prepare quaternary ammonium intermediate 1;
(2) Preparation of quaternary ammonium intermediate 2
(2-i) Compound b-1 reacts with compound $R_4$-Br to prepare compound b-2;
(2-ii) Compound b-2 reacts with the coupling molecule to prepare quaternary ammonium intermediate 2;

(3) Quaternary ammonium intermediate 1 reacts with quaternary ammonium intermediate 2, to prepare the dicationic compound;

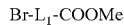

In which, compound a-1 is

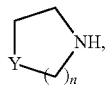   a-1 compound a-2 is a-2 compound a-3 is

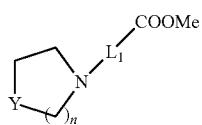   a-3 compound a-4 is

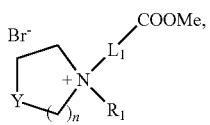   a-4 quaternary ammonium intermediate 1

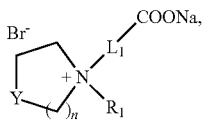

Quaternary ammonium intermediate 1 compound b-1 is

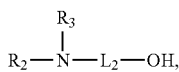   b-1 compound b-2 is

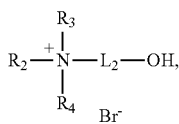   b-2 the coupling molecule is

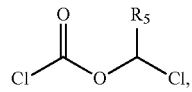   a-2 quaternary ammonium intermediate 2 is

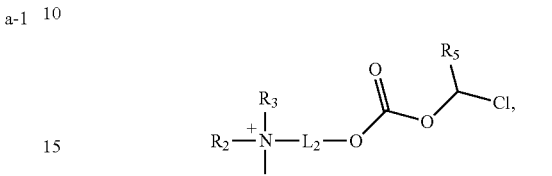   a-3

Quaternary ammonium intermediate 2 and the dicationic compound is

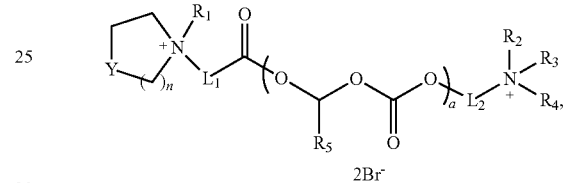   a-4

N, Y, $L_1$, $L_2$, $R_1$, $R_2$, $R_3$, $R_4$, and $R_5$ are as stated above.

The present invention further provides the use of the bicationic compound mentioned above, or the stereoisomer or the stereoisomer mixture, or the pharmaceutically acceptable salt, or the solvate, or the crystal thereof, in the preparation of muscle relaxants.

The present invention further provides a muscle relaxant, characterized in that it is prepared by using the bicationic compound mentioned above, or the stereoisomer or the stereoisomer mixture, or the pharmaceutically acceptable salt, or the solvate, or the crystal thereof as active ingredients, with the addition of pharmaceutically acceptable adjuvents.

The compound of the present invention has a rapid effect after single administration, and provides 2-10 min of complete muscle relaxation. These compounds only need to rely on the body's own metabolism, and can achieve ultra-short-acting and non-depolarizing muscle relaxation. After exerting ultra-short-acting effect on muscle relaxation, it is cleared up quickly by itself. The experiment has shown that the compounds of the present invention have the characteristics of rapid onset and rapid recovery, compared with the positive control drugs cisatracurium and succinylcholine, and are a typical non-depolarizing muscle relaxant.

Based on above-mentioned characteristics, compounds with the structure of formula (I), the stereoisomers or the mixtures of stereoisomers, or the pharmaceutically acceptable salts, or the solvates or the co-crystals and the combinations thereof, and their combinations with pharmaceutically acceptable carriers can be used in the field of preparation of muscle relaxants, to provide fast, ultra-short-acting, and non-depolarizing muscle relaxant meeting the clinical needs. For the definition of term used in the present invention: unless otherwise specified, the initial definition provided for the group or the term herein is applicable to those in the whole specification; for terms not specifically defined herein, according to the disclosure content and the context, the term should have the meaning commonly given by those skilled in the field.

The minimum and maximum values of carbon atom content in the hydrocarbon group are indicated by a prefix, for example, the prefix ($C_a$-$C_b$)alkyl indicates any alkyl group having "a"-"b" carbon atoms. Therefore, for example, ($C_1$-$C_6$)alkyl means an alkyl containing 1-6 carbon atoms.

Said $C_1$-$C_6$ alkyl denotes $C_1$, $C_2$, $C_3$, $C_4$, $C_5$, $C_6$ alkyl, that is linear or branched alkyl having 1-6 carbon atoms, such as methyl, ethyl, propyl, isopropyl, butyl, isobutyl, tert-butyl, sec-butyl, pentyl, hexyl, etc.

In said

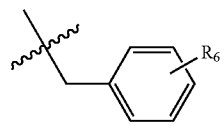

of the present invention, $R_6$ is selected from one or more H, nitros, halogens, methoxys, hydroxyls, cyanos, $C_1$-$C_3$ alkyls, phenyls, and trifluoromethyls, that means in

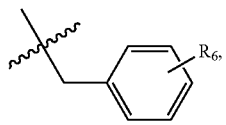

there are one or more substituents ($R_6$), and when there are two or more substituents, two or more $R_6$ are independently of each other selected from H, nitros, halogens, methoxys, hydroxyls, cyanos, $C_1$-$C_3$ alkyls, phenyls, and trifluoromethyls.

The cycloalkyl denotes cyclic alkyl, such as cyclopropyl, cyclobutyl, cyclopentyl, cyclohexyl, etc.

Obviously, based on above content of the present invention, according to the common technical knowledge and the conventional means in the field, without department from above basic technical spirits, other various modifications, alternations or changes can further be made.

By following specific examples of said embodiments, above content of the present invention is further illustrated. But it should not be construed that the scope of above subject of the present invention is limited to following examples. The techniques realized based on above content of the present invention are all within the scope of the present invention.

EXAMPLES

Example 1 Preparation of Compound 1

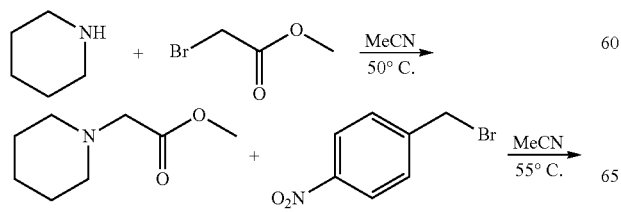

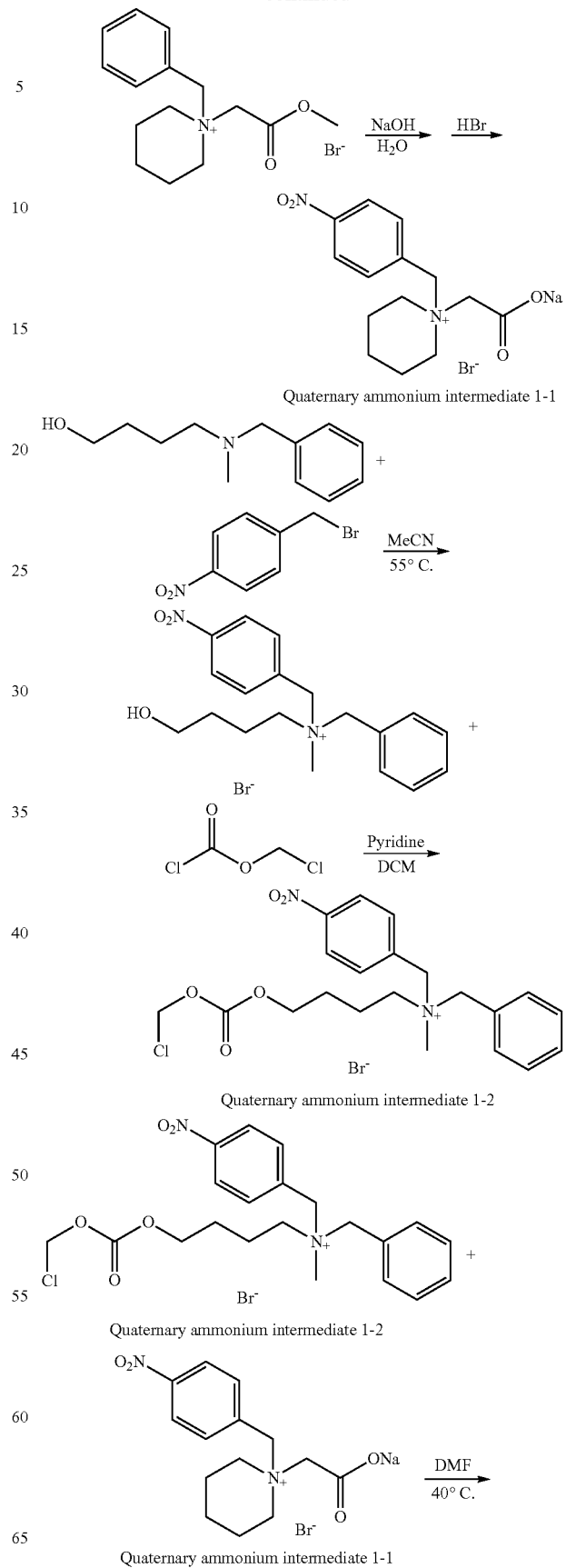

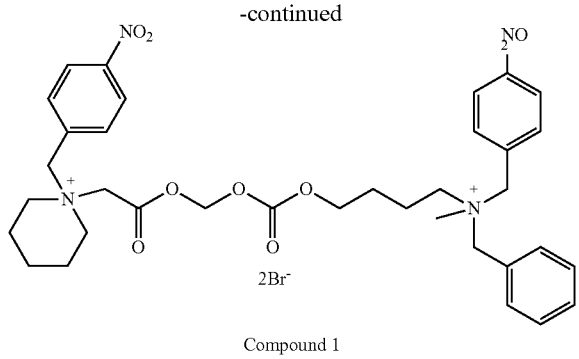

Compound 1

Methyl 2-bromoacetate (1.53 g) was dissolved in 30 mL acetonitrile, to which were added 0.85 g piperidine and 1.38 g anhydrous potassium carbonate. The mixture was stirred at 50° C. for 10 hours, and then p-nitrobenzyl bromide (2.16 g) was added. The reaction was further stirred at 55° C. for 6 hours, and filtered, then the solvent was evaporated under reduced pressure. To the residue, was added 2N sodium hydroxide aqueous solution (40 mL), and the resultant solution was stirred at room temperature for 2 hours, then pH value was adjusted to 9 with hydrobromic acid aqueous solution. The solvent was evaporated to dryness under reduced pressure, and then 50 mL dichloromethane was added to the residue. The mixture was heated to a slight boiling, and filtered while hot. The filtrate was evaporated to dryness to obtain bright yellow crude product of intermediate (1-1) (1.71 g).

4-Hydroxybutyl-methyl-benzylamine (1.93 g) was dissolved in 30 mL acetonitrile, to which was added p-nitrobenzyl bromide (2.16 g), and then stirred for 8 hours at 55° C. The solvent was evaporated to dryness under reduced pressure, and yellow solid was precipitated. The solid was dissolved in 50 mL dichloromethane, and then 1.6 g pyridine was added. The mixture was cooled to 5° C., and 1.3 g chloromethyl chloroformate was added. After addition, the mixture was stirred for 3 hours at room temperature. The solvent was evaporated to dryness under reduced pressure, and then the residue was subjected to column chromatography to provide 1.32 g intermediate (1-2).

Intermediate 1-2 (1.32 g) and intermediate 1-1 (1.0 g) were dissolved in 50 mL acetonitrile, and stirred at 40° C. for 12 hours, then the solvent was evaporated to dryness under reduced pressure.

The residue was separated by reversed-phase preparative chromatography, to provide white powder (0.53 g), i.e. compound 1, with a yield of 23.5%.

$^1$HNMR (DMSO-$d_6$, 400 MHz) δ:1.52-1.56 (2H, m), 1.61-1.84 (8H, m), 3.01 (3H, s), 3.13-3.24 (4H, m), 3.41-3.43 (2H, m), 3.65-3.74 (2H, m), 4.51 (1H, d, J=12.8 Hz), 4.67-4.77 (5H, m), 4.85 (1H, d, J=12.8 Hz), 4.96 (1H, d, J=12.8 Hz), 5.74 (2H, s), 7.52-7.55 (3H, m), 7.62-7.64 (2H, m), 7.75-7.77 (2H, m), 7.96-7.98 (2H, m), 8.28-8.36 (4H, m).

Example 2 Preparation of Compound 2

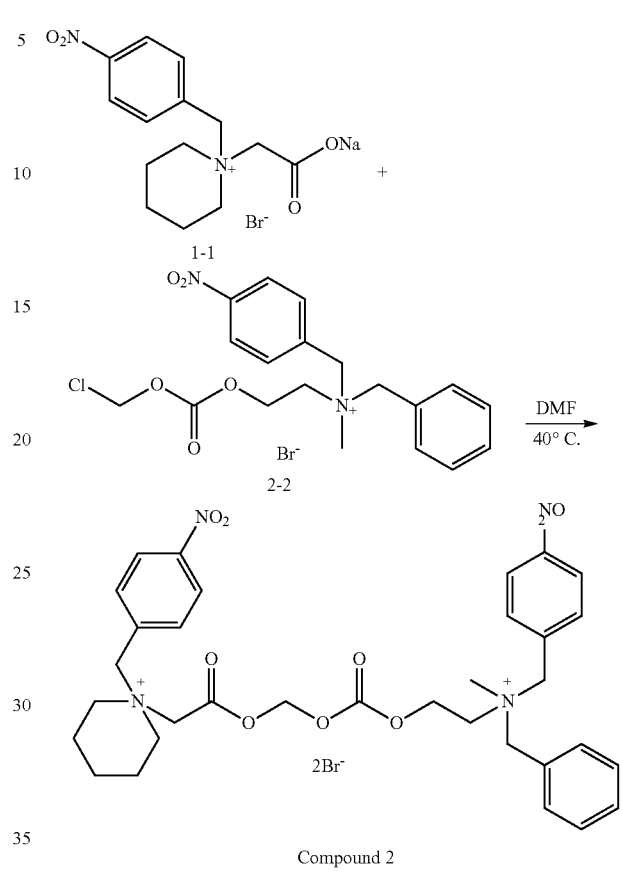

Compound 2

Quaternary ammonium intermediates 1-1 and 2-2 were prepared by referring to Example 1. Intermediate 1-1 (1.91 g) and intermediate 2-2 (2.36 g) were dissolved in 50 mL acetonitrile, and stirred at 40° C. for 12 hours, then the solvent was evaporated to dryness under reduced pressure. The residue was separated by preparative chromatography, to provide white powder (1.03 g), i.e. compound 2, with a yield of 25.9%.

$^1$HNMR (DMSO-$d_6$, 400 MHz) δ: 1.58-1.59 (2H, m), 1.92 (4H, s, broad), 3.06 (3H, s), 3.51-3.53 (3H, m), 3.71-3.76 (3H, m), 4.52-4.55 (3H, m), 4.75-4.77 (3H, m), 4.90-5.08 (4H, m), 5.86 (2H, s), 7.51-7.55 (3H, m), 7.61-7.62 (2H, m), 7.75-7.77 (2H, m), 7.95-7.96 (2H, m), 8.29-8.36 (4H, m).

Example 3 Preparation of Compound 3

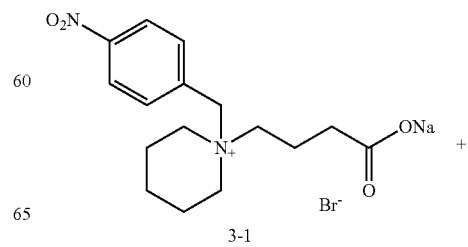

-continued

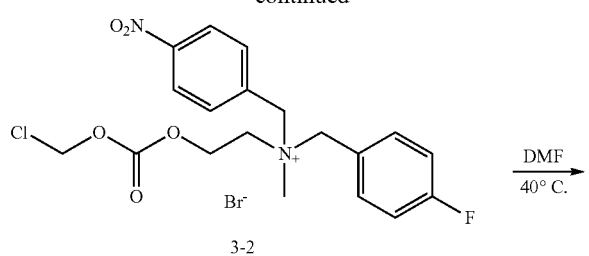

3-2

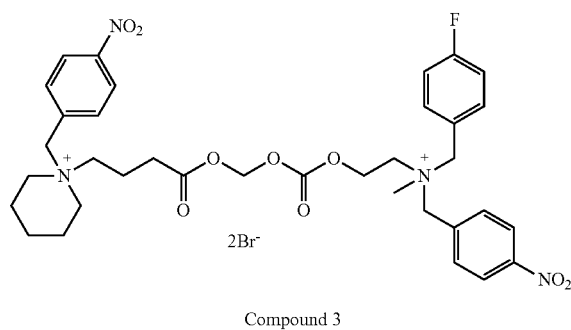

Compound 3

Quaternary ammonium intermediates 3-1 and 3-2 were prepared by referring to Example 1. Intermediate 3-1 (2.05 g) and intermediate 3-2 (2.95 g) were dissolved in 50 mL acetonitrile, and stirred at 40° C. for 12 hours, then the solvent was evaporated to dryness under reduced pressure. The residue was separated by preparative chromatography, to provide white powder (1.1 g), i.e. compound 3, with a yield of 25.7%.

$^1$HNMR (DMSO-$d_6$, 400 MHz) δ: 1.43 (1H, s, broad), 1.60-1.64 (1H, m), 1.83 (4H, s, broad), 2.08 (2H, s, broad), 2.57-2.61 (2H, m), 3.04 (3, s), 3.23-3.28 (3H, m), 3.41-3.44 (3K, m), 3.67 (2H, s), 4.54-4.57 (1H, m), 4.68-4.78 (5H, m), 4.91-5.03 (2H, m), 5.78 (2H, s), 7.36-7.40 (2H, m), 7.67-7.71 (2H, m), 7.85-7.95 (4H, m), 8.32-8.38 (4H, m).

Example 4 Preparation of Compound 4

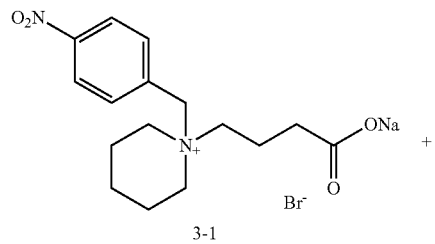

3-1

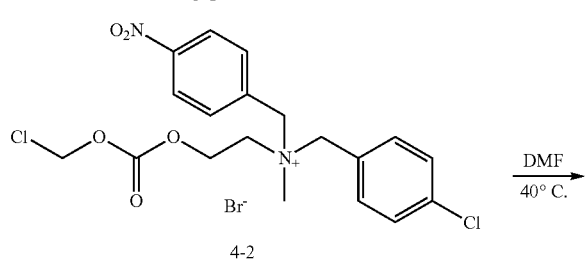

4-2

-continued

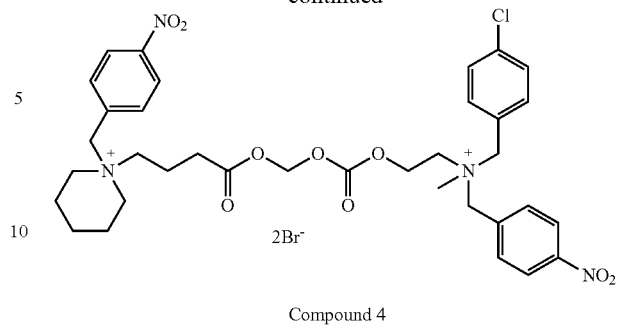

Compound 4

Quaternary ammonium intermediates 3-1 and 4-2 were prepared by referring to Example 1. Intermediate 3-1 (2.05 g) and intermediate 4-2 (2.51 g) were dissolved in 50 mL acetonitrile, and stirred at 40° C. for 12 hours, then the solvent was evaporated to dryness under reduced pressure.

The residue was separated by preparative chromatography, to provide white powder (1.19 g), i.e. compound 4, with a yield of 27.2%.

$^1$HNMR (DMSO-$d_6$, 400 MHz) δ: 1.42 (1H, s, broad), 1.60 (1H, s, broad), 1.83-1.88 (4H, m), 2.08-2.09 (2H, m), 2.57-2.60 (2H, m), 3.05 (3H, s), 3.24-3.33 (4H, m), 3.41-3.44 (2H, m), 2.68 (2H, s, broad), 4.57 (11H, d, J=12.0 Hz), 4.69-4.78 (5H, m), 4.93 (H, d, J=12.0 Hz), 5.03 (1H, d, J=12.0 Hz), 5.77 (2H, s), 7.58-7.67 (4H, m), 7.84-7.95 (4H, m), 8.31-8.36 (4H, m).

Example 5 Preparation of Compound 5

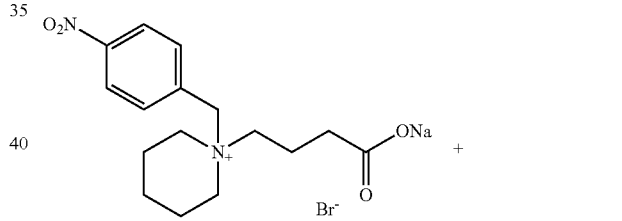

3-1

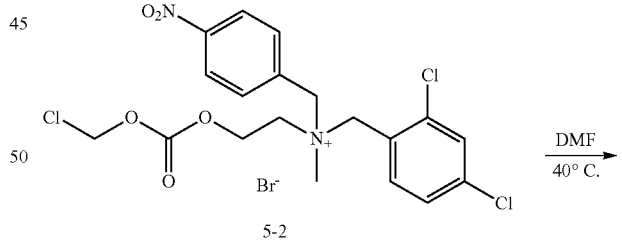

5-2

Compound 5

Quaternary ammonium intermediates 3-1 and 5-2 were prepared by referring to Example 1. Intermediate 3-1 (2.05 g) and intermediate 5-2 (2.71 g) were dissolved in 50 mL acetonitrile, and stirred at 40° C. for 12 hours, then the solvent was evaporated to dryness under reduced pressure.

The residue was separated by preparative chromatography, to provide white powder (1.02 g), i.e. compound 5, with a yield of 20.6%.

¹HNMR (DMSO-d₆, 400 MHz) δ: 1.41 (1H, s, broad), 1.60 (1H, s, broad), 1.83 (4H, s, broad), 2.07 (2H, s, broad), 2.55-2.65 (2H, m), 3.05 (3H, s), 3.22-3.26 (4H, m), 3.39-3.42 (2H, m), 3.72-3.81 (2H, m), 4.59-4.62 (1H, m), 4.67-4.78 (5H, m), 4.91-4.99 (2H, m), 5.77 (2H, s), 7.64-7.65 (1H, m), 7.82-7.96 (6H, m), 8.33-8.38 (4H, m).

Example 6 Preparation of Compound 6

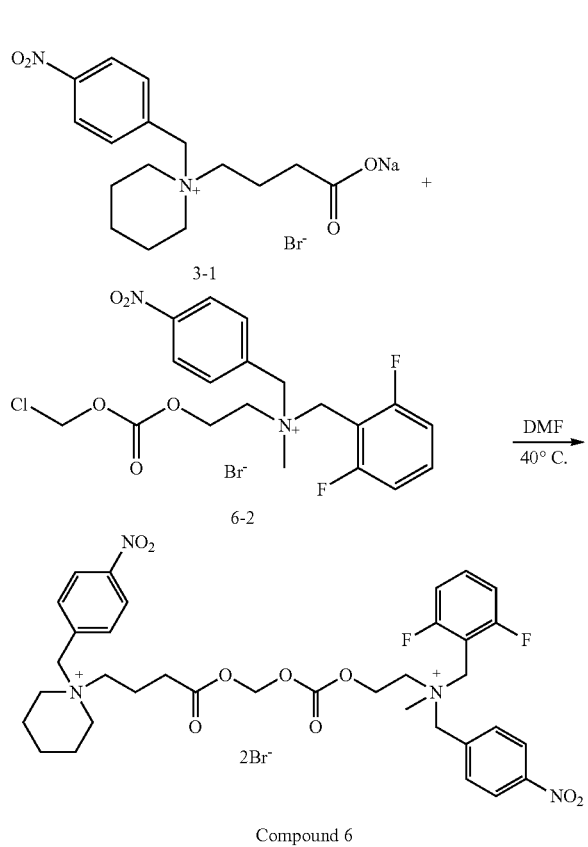

Quaternary ammonium intermediates 3-1 and 6-2 were prepared by referring to Example 1. Intermediate 3-1 (2.05 g) and intermediate 6-2 (2.71 g) were dissolved in 50 mL acetonitrile, and stirred at 40° C. for 12 hours, then the solvent was evaporated to dryness under reduced pressure.

The residue was separated by preparative chromatography, to provide white powder (0.75 g), i.e. compound 6, with a yield of 17.4%.

¹HNMR (DMSO-d₆, 400 MHz) δ: 1.44 (1H, s, broad), 1.60 (1H, s, broad), 1.84 (4H, s, broad), 2.05 (2H, s, broad), 2.56-2.59 (2H, m), 3.05 (3H, s), 3.22-3.28 (3H, m), 3.41-3.45 (3H, m), 3.70-3.73 (1H, m), 3.85-3.88 (1H, m), 4.54-4.58 (1H, m), 4.77 (4H, s, broad), 4.90-5.00 (3H, m), 5.78 (2H, s), 7.31-7.36 (2K, m), 7.72-7.76 (1H, m), 7.84-7.86 (2H, m), 7.99-8.01 (2, m), 8.32-8.38 (4H, m).

Example 7 Preparation of Compound 7

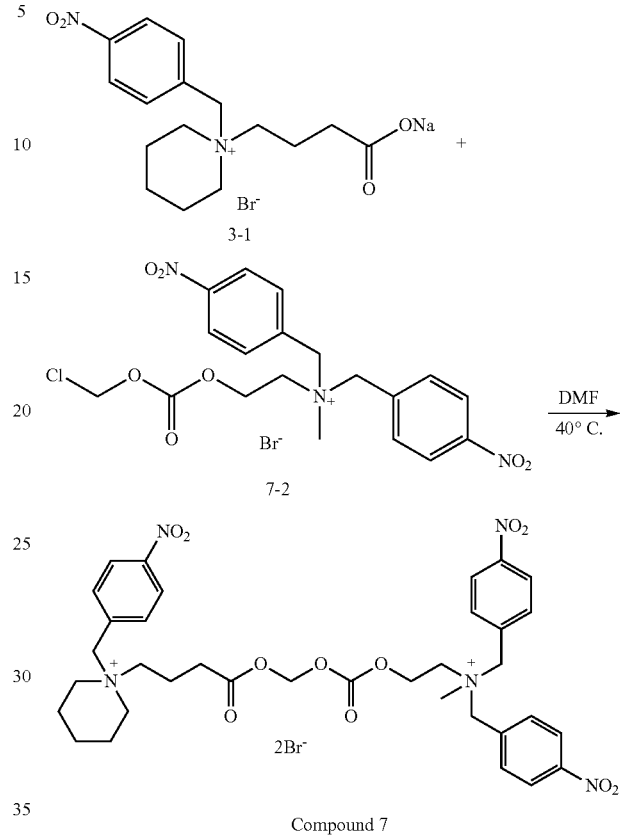

Quaternary ammonium intermediates 3-1 and 7-2 were prepared by referring to Example 1. Intermediate 3-1 (2.05 g) and intermediate 7-2 (2.59 g) were dissolved in 50 mL acetonitrile, and stirred at 40° C. for 12 hours, then the solvent was evaporated to dryness under reduced pressure. The residue was separated by preparative chromatography, to provide white powder (1.13 g), i.e. compound 7, with a yield of 26.0%. ¹HNMR (DMSO-d₆, 400 MHz) δ: 1.43 (1H, s, broad), 1.60 (1H, s, broad), 1.84 (4H, s, broad), 2.08 (2H, s, broad), 2.57-2.60 (2H, m), 3.10 (3H, s), 3.25-3.29 (2H, m), 3.42-3.44 (4H, m), 3.73 (2H, s, broad), 4.72-4.77 (6n, m), 5.08 (2H, s, broad), 5.78 (2H, s), 7.85-7.87 (2H, m), 7.94-7.95 (4H, m), 8.32-8.38 (6H, m).

Example 8 Preparation of Compound 8

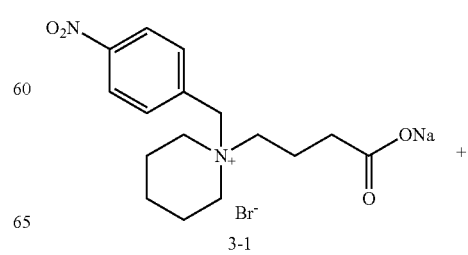

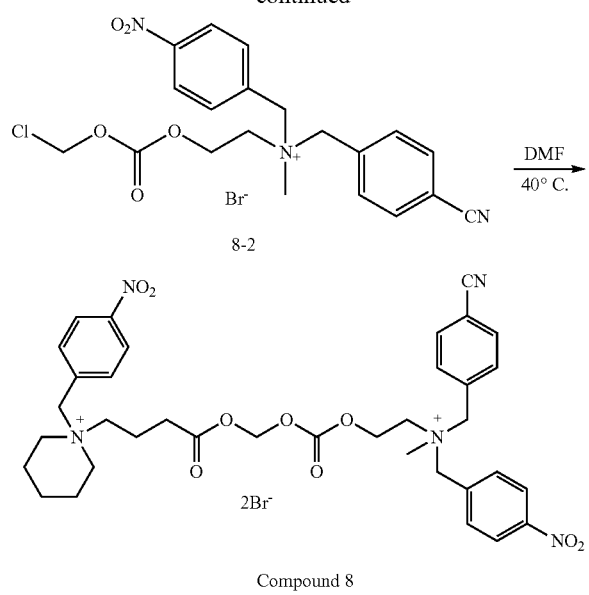

8-2

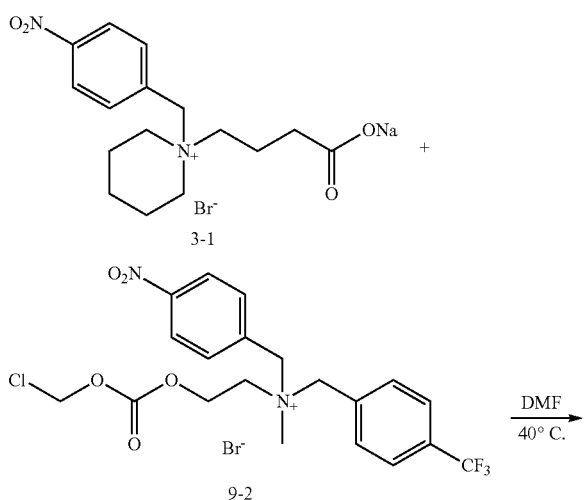

2Br⁻

Compound 8

Quaternary ammonium intermediates 2-1 and 13-2 were prepared by referring to Example 1. Intermediate 3-1 (2.05 g) and intermediate 8-2 (2.5 g) were dissolved in 50 mL acetonitrile, and stirred at 40° C. for 12 hours, then the solvent was evaporated to dryness under reduced pressure. The residue was separated by preparative chromatography, to provide white powder (0.69 g), i.e. compound 8, with a yield of 16.2%.

¹HNMR (DMSO-d₆, 400 MHz) δ: 1.43 (1H, s, broad), 1.60-1.63 (1H, m), 1.83 (4H, s, broad), 2.08-2.09 (2H, m), 2.53-2.59 (2H, m), 3.08 (3H, s), 3.25-3.28 (4H, m), 3.41-3.44 (2H, m), 3.70 (2H, s, broad), 4.65-4.78 (6H, m), 5.03-5.10 (2H, m), 5.78 (2H, s), 7.85-7.86 (4H, m), 7.93-7.95 (2H, m), 8.02-8.04 (2H, m), 8.32-8.37 (4H, m).

Example 9 Preparation of Compound 9

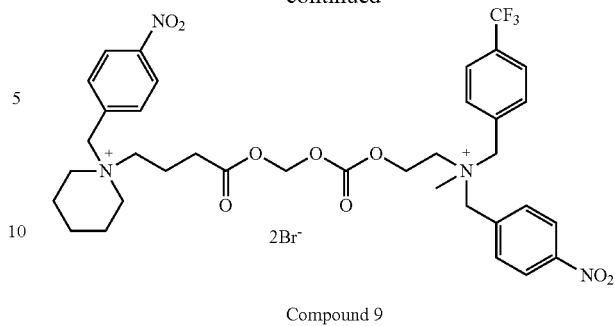

Compound 9

Quaternary ammonium intermediates 3-1 and 9-2 were prepared by referring to Example 1. Intermediate 3-1 (2.05 g) and intermediate 9-2 (2.7 g) were dissolved in 50 mL acetonitrile, and stirred at 40° C. for 12 hours, then the solvent was evaporated to dryness under reduced pressure. The residue was separated by preparative chromatography, to provide white powder (0.73 g), i.e. compound 9, with a yield of 16.4%.

¹HNMR (DMSO-d₆, 400 MHz) δ: 1.43 (1H, s, broad), 1.60-1.63 (1H, m), 1.83 (4H, s, broad), 2.08-2.09 (2H, m), 2.57-2.61 (2H, m), 3.09 (3H, s), 3.24-3.44 (6H, m), 3.71-3.75 (2H, m), 4.65-4.78 (6H, m), 4.94-5.09 (2H, m), 5.78 (2H, s), 7.85-7.96 (8H, m), 8.33-8.39 (4H, m).

Example 10 Preparation of Compound 10

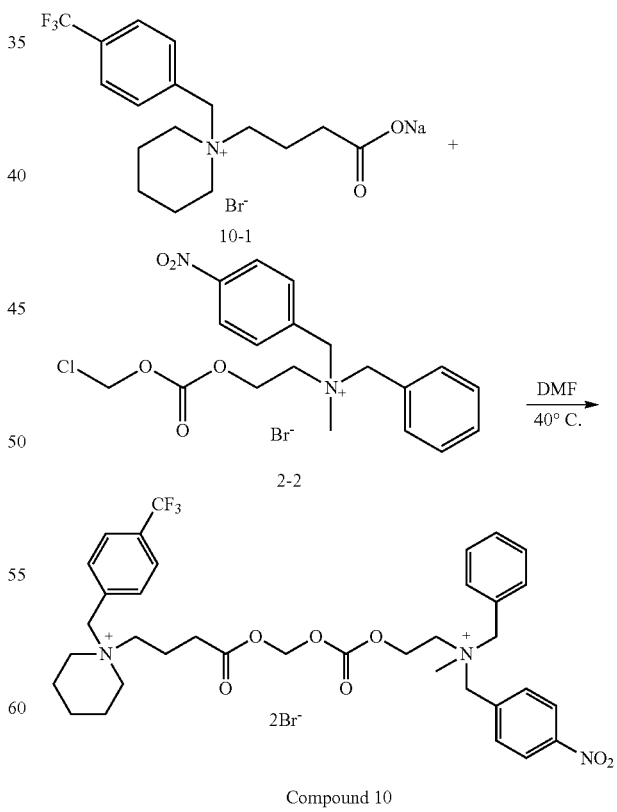

Compound 10

Quaternary ammonium intermediates 10-1 and 2-2 were prepared by referring to Example 1. Intermediate 10-1 (2.16 g) and intermediate 2-2 (2.37 g) were dissolved in 50 mL acetonitrile, and stirred at 40° C. for 12 hours, then the solvent was evaporated to dryness under reduced pressure. The residue was separated by preparative chromatography, to provide white powder (0.88 g), i.e. compound 10, with a yield of 20.8%.

¹HNMR (DMSO-d$_6$, 400 MHz) δ: 1.44 (1H, s, broad), 1.61 (1H, s, broad), 1.84 (4H, s, broad), 2.1 (2H, m), 2.58-2.59 (2H, m), 3.06 (3H, s), 3.26-3.29 (3H, m), 3.41-3.44 (3H, m), 3.69 (2H, s, broad), 4.55-4.58 (1H, m), 4.74 (5H, s, broad), 4.94-5.08 (2H, m), 5.78 (2H, s), 7.53-7.63 (5H, m), 7.80-7.99 (6H, m), 8.36-8.38 (2H, m).

Example 11 Preparation of Compound 11

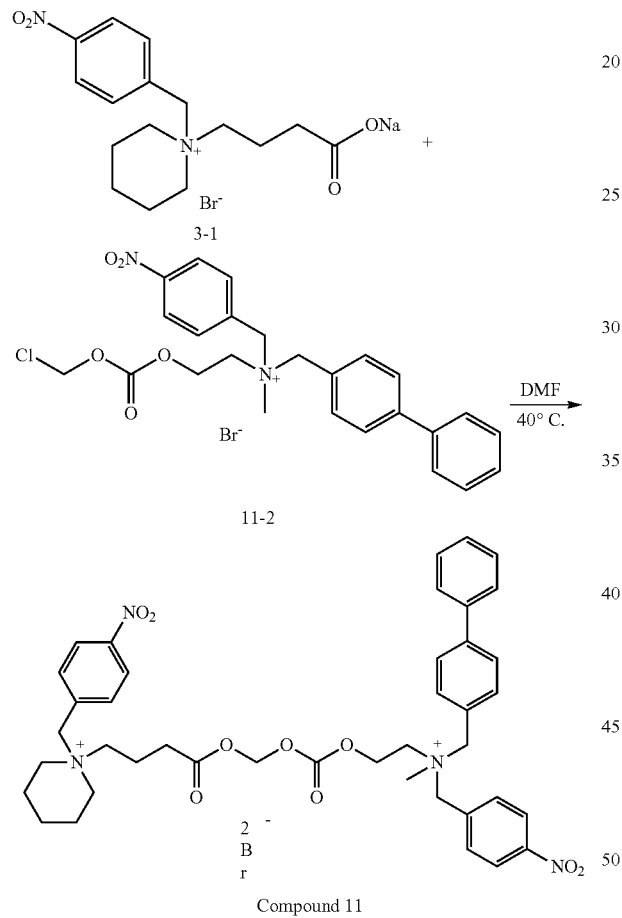

Compound 11

5.79 (2H, s), 7.41-7.45 (11H, m), 7.49-7.53 (2H, m), 7.69-7.75 (4H, m), 7.83-7.86 (4H, m), 7.94-7.96 (2H, m), 8.33-8.40 (4H, m).

Example 12 Preparation of Compound 12

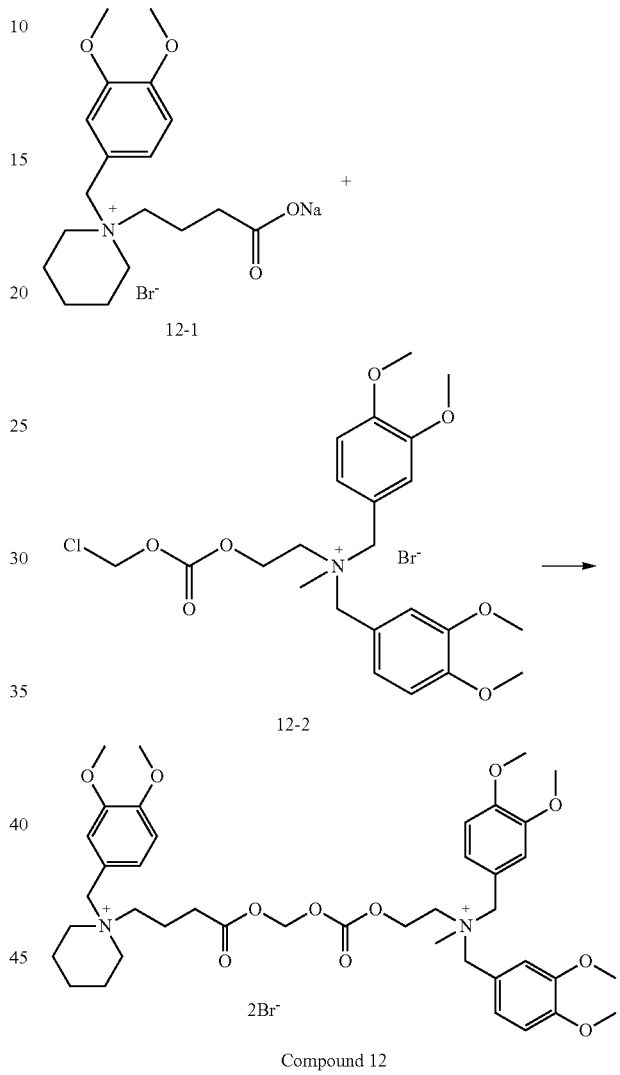

Compound 12

Quaternary ammonium intermediates 3-1 and 11-2 were prepared by referring to Example 1. Intermediate 3-1 (2.05 g) and intermediate 11-2 (2.75 g) were dissolved in 50 mL acetonitrile, and stirred at 40° C. for 12 hours, then the solvent was evaporated to dryness under reduced pressure. The residue was separated by preparative chromatography, to provide white powder (1.16 g), i.e. compound 11, with a yield of 25.1%.

¹HNMR (DMSO-d$_6$, 400 MHz) δ: 1.43 (1H, s, broad), 1.60 (1H, s, broad), 1.84 (4H, s, broad), 2.33-2.34 (2H, m), 2.51-2.53 (2H, m), 3.07 (3H, s), 3.19-3.28 (4H, m), 3.39-3.42 (2H, m), 3.69 (2H, s, broad), 4.55-4.58 (1H, m), 4.71-4.76 (5H, m), 4.86-4.89 (1H, m), 4.96-4.99 (1H, m), Quaternary ammonium intermediates 12-1 and 12-2 were prepared by referring to Example 1. Intermediate 12-1 (2.12 g) and intermediate 12-2 (2.74 g) were dissolved in 50 mL acetonitrile, and stirred at 40° C. for 10 hours, then the solvent was evaporated to dryness under reduced pressure. The residue was separated by preparative chromatography, to provide white powder (1.04 g), i.e. compound 12, with a yield of 22.7%.

¹HNMR (DMSO-d$_6$, 400 MHz) δ: 1.45-1.30 (m, 1H), 1.70-1.55 (m, 1H), 1.90-1.75 (m, 4H), 2.07-1.95 (m, 2H), 2.65-2.55 (m, 2H), 3.01 (s, 3H), 3.41-3.31 (m, 2H), 3.63 (d, J=13.2 Hz, 2H), 3.79 (s, 18H), 3.92 (s, 3H), 4.63-4.43 (m, 4H), 4.88-4.67 (m, 4H), 5.76 (s, 2H), 7.06 (d, J=6.4 Hz, 4H), 7.27 (s, 2H), 7.18 (s, 3H).

Example 13 Preparation of Compound 13

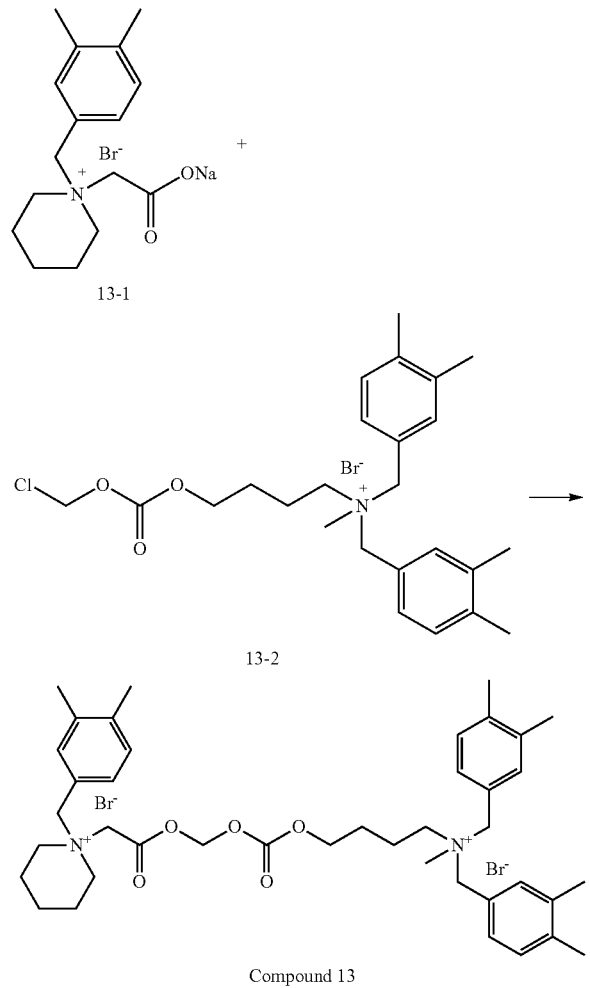

13-1

13-2

Compound 13

Quaternary ammonium intermediates 13-1 and 13-2 were prepared by referring to Example 1. Intermediate 13-1 (1.82 g) and intermediate 13-2 (2.56 g) were dissolved in 50 mL acetonitrile, and stirred at 40° C. for 12 hours, then the solvent was evaporated to dryness under reduced pressure. The residue was separated by preparative chromatography, to provide white powder (1.07 g), i.e. compound 13, with a yield of 26.1%.

$^1$HNMR (DMSO-$d_6$, 400 MHz) δ: 1.69-1.50 (m, 4H), 2.03-1.86 (m, 6H), 2.26 (d, J=4.4 Hz, 18H), 2.88-2.78 (m, 3H), 3.15-3.01 (m, 2H), 3.58-3.46 (m, 2H), 3.71 (d, J=12.4 Hz, 2H), 4.24 (t, J=6.4 Hz, 2H), 4.47-4.34 (m, 4H), 4.60-4.51 (m, 2H), 5.87 (s, 2H), 4.72 (s, 2H), 7.20-7.13 (m, 2H), 7.27 (td, J=8.0, 15.2 Hz, 5H), 7.34 (s, 2H).

Example 14 Preparation of Compound 14

By referring to Example 1, methyl 2-bromoacetate and p-nitrobenzyl bromide used in the synthesis of quaternary ammonium intermediates 1-1 and 1-2 were replaced with methyl 2-chloroacetate and p-nitrobenzyl chloride, which can ensure that the anion of the final target compound (I) is Cl$^-$, i.e. compound 14.

Example 15 Preparation of Compound 15

Compound 14 (100 mg) was dissolved in 300 mL water, to which was drop added the aqueous solution of silver p-toluenesulfonate (40 mg) under stirring. The precipitate was removed by filtration. After the filtrate was lyophilized, 109 mg of target compound (I) containing the anion p-toluenesulfonate was obtained, i.e. compound 15.

Example 16. Synthesis of Other Compounds

For other compounds disclosed in this patent, the synthetic method could refer to the preparative method described in Example 1, and the quaternary ammonium intermediates 1 and 2 were synthesized, respectively. Both of intermediates were dissolved in nonprotonic polar solvents such as DMF or acetonitrile and the like, and then heated and stirred at the temperature of r.t.-80° C. for 6-24 hours, followed by separation and purification, to obtain the target compounds. The structures and mass spectra of preferred compounds are shown in Table 1.

TABLE 1

The structures and mass spectra of part of preferred compounds

| Compound No. | Structure | [M]$^{2+}$ (without anion) |
|---|---|---|
| Compound 17 | 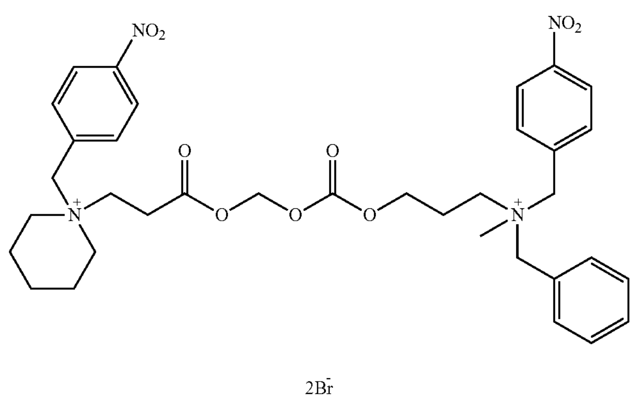 | 332.1 |

TABLE 1-continued
The structures and mass spectra of part of preferred compounds
| Compound No. | Structure | $[M]^{2+}$ (without anion) |
|---|---|---|
| Compound 18 | 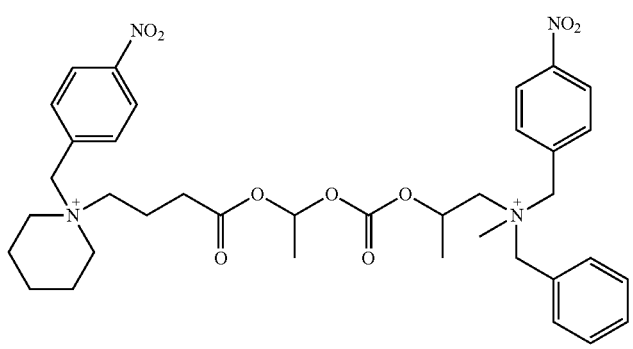 2Br⁻ | 346.1 |
| Compound 19 | 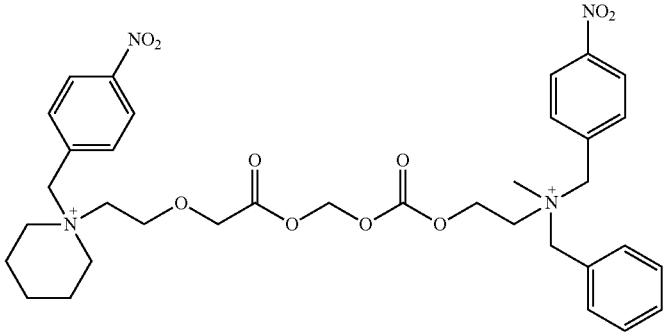 2Br⁻ | 340.1 |
| Compound 20 | 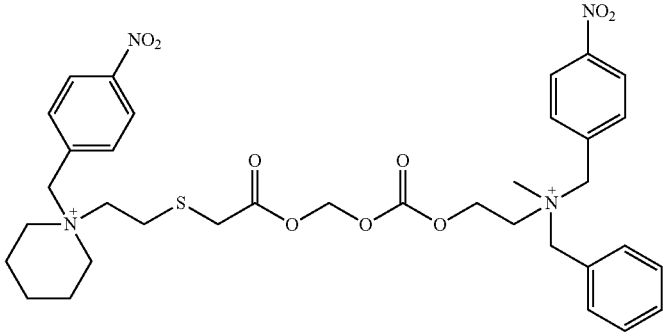 2Br⁻ | 348.1 |

TABLE 1-continued

The structures and mass spectra of part of preferred compounds

| Compound No. | Structure | [M]²⁺ (without anion) |
|---|---|---|
| Compound 21 | (structure shown) 2Br⁻ | 354.1 |
| Compound 22 | (structure shown) 2Br⁻ | 347.1 |
| Compound 23 | (structure shown) 2Br⁻ | 355.1 |

TABLE 1-continued

The structures and mass spectra of part of preferred compounds

| Compound No. | Structure | [M]²⁺ (without anion) |
|---|---|---|
| Compound 24 | (structure shown) 2Br⁻ | 325.1 |
| Compound 25 | (structure shown) 2Br⁻ | 410.1 |
| Compound 26 | (structure shown) 2Br⁻ | 387.5 |

TABLE 1-continued

The structures and mass spectra of part of preferred compounds

| Compound No. | Structure | [M]²⁺ (without anion) |
| --- | --- | --- |
| Compound 27 | 2Br⁻ | 343.6 |
| Compound 28 | 2Br⁻ | 369.6 |
| Compound 29 | 2Br⁻ | 362.1 |

TABLE 1-continued

The structures and mass spectra of part of preferred compounds

| Compound No. | Structure | [M]²⁺ (without anion) |
|---|---|---|
| Compound 30 | 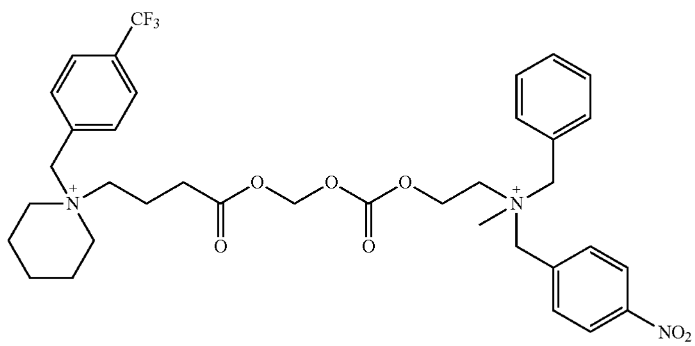 | 343.6 |
| Compound 31 | 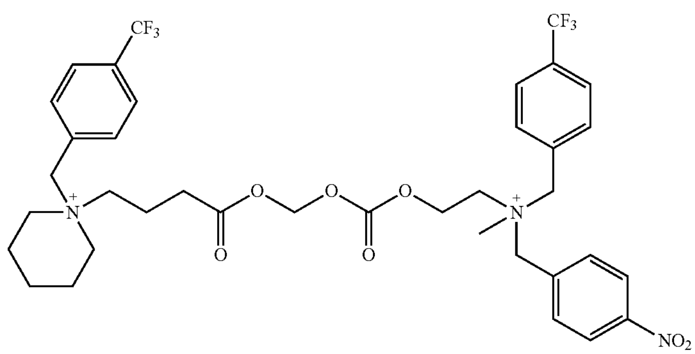 | 377.6 |
| Compound 32 | 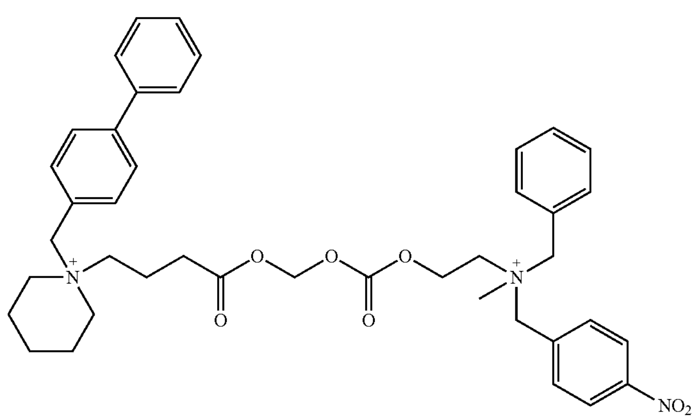 | 347.6 |

TABLE 1-continued

The structures and mass spectra of part of preferred compounds

| Compound No. | Structure | [M]²⁺ (without anion) |
|---|---|---|
| Compound 33 | 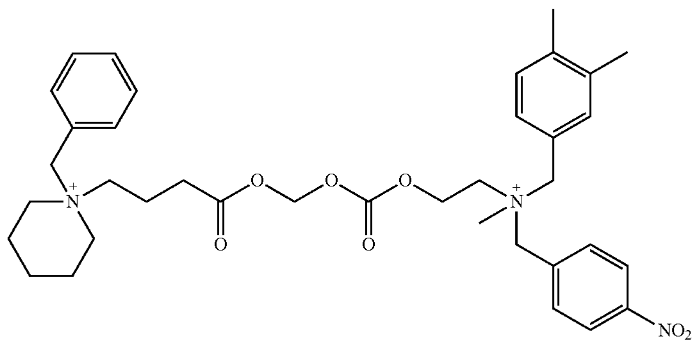 | 323.6 |
| Compound 34 | 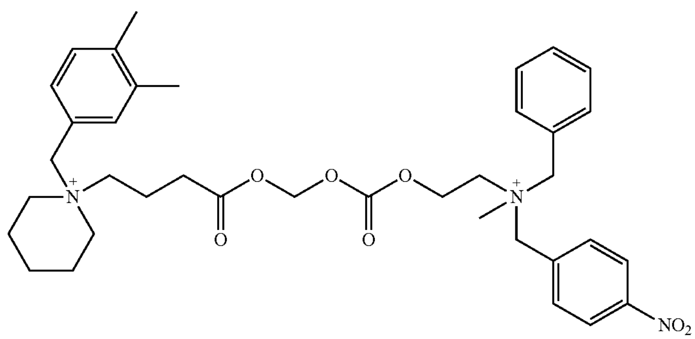 | 323.6 |
| Compound 35 | 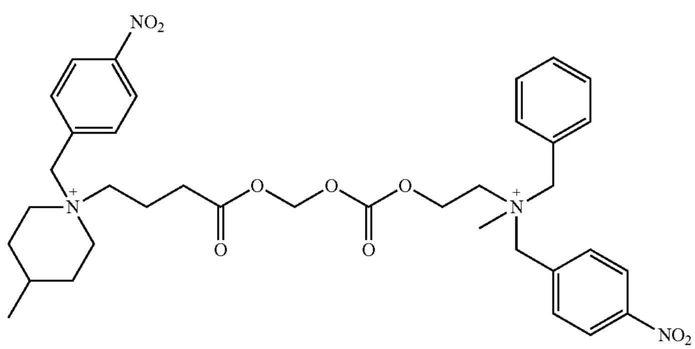 | 339.1 |
| Compound 36 | 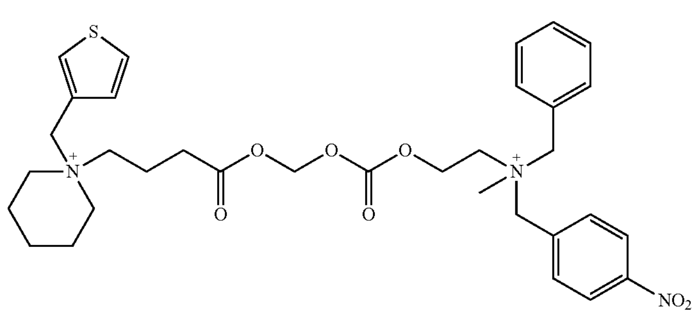 | 312.6 |

TABLE 1-continued
The structures and mass spectra of part of preferred compounds
| Compound No. | Structure | [M]²⁺ (without anion) |
|---|---|---|
| Compound 37 | 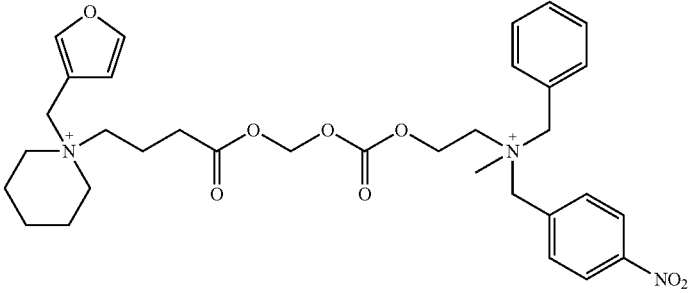 2Br⁻ | 304.6 |
| Compound 38 | 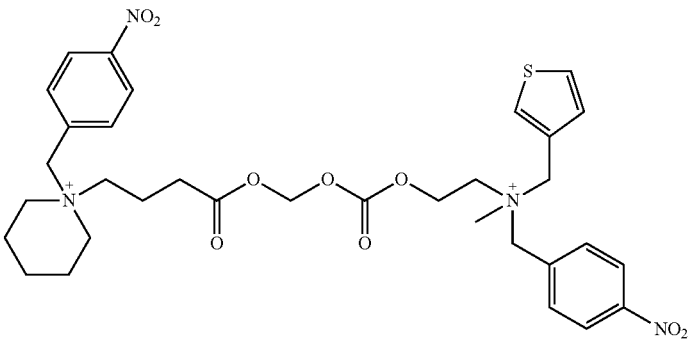 2Br⁻ | 335.1 |
| Compound 39 | 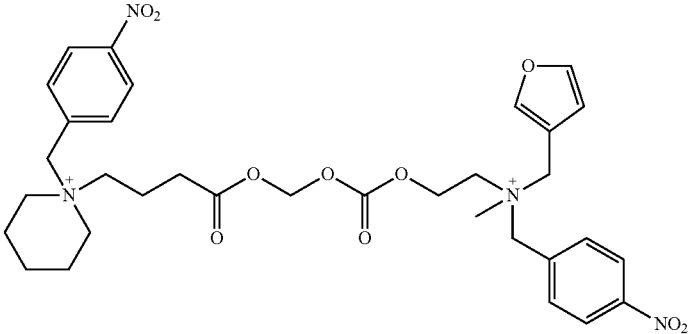 2Br⁻ | 327.1 |
| Compound 40 | 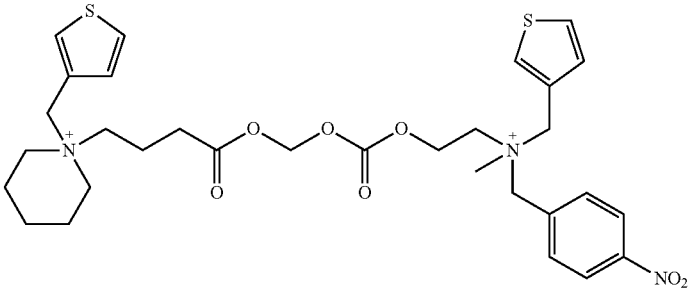 2Br⁻ | 315.6 |

TABLE 1-continued

The structures and mass spectra of part of preferred compounds

| Compound No. | Structure | [M]²⁺ (without anion) |
|---|---|---|
| Compound 41 | 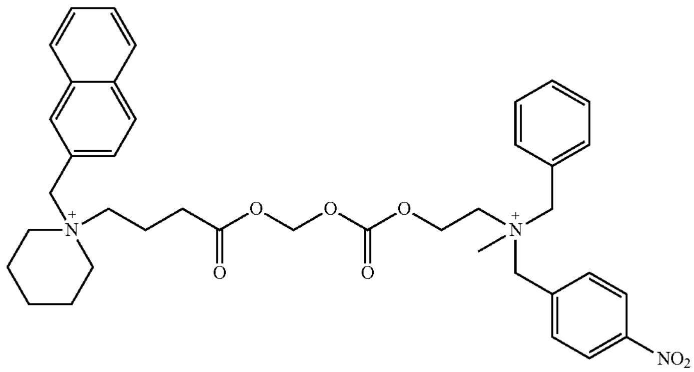 | 334.6 |
| Compound 42 | 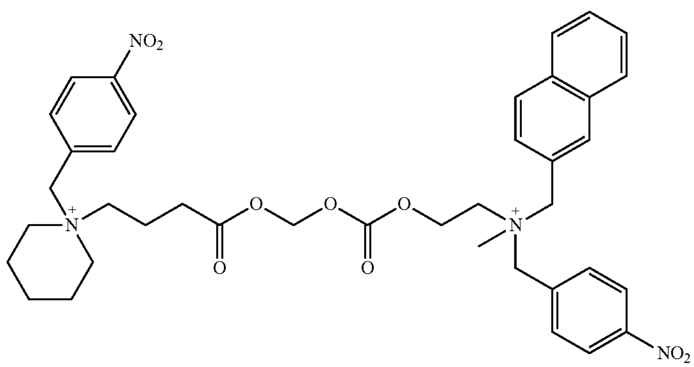 | 357.1 |
| Compound 43 | 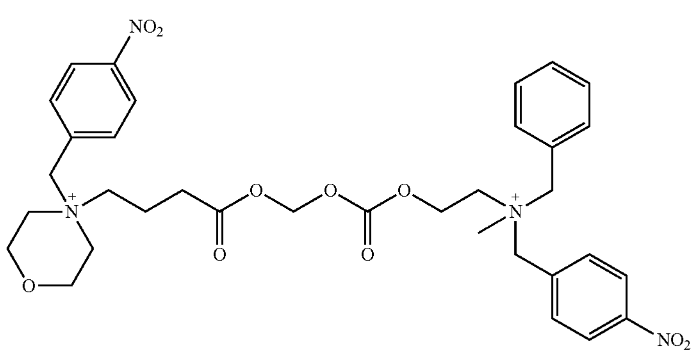 | 333.1 |

TABLE 1-continued
The structures and mass spectra of part of preferred compounds
| Compound No. | Structure | [M]²⁺ (without anion) |
|---|---|---|
| Compound 44 | 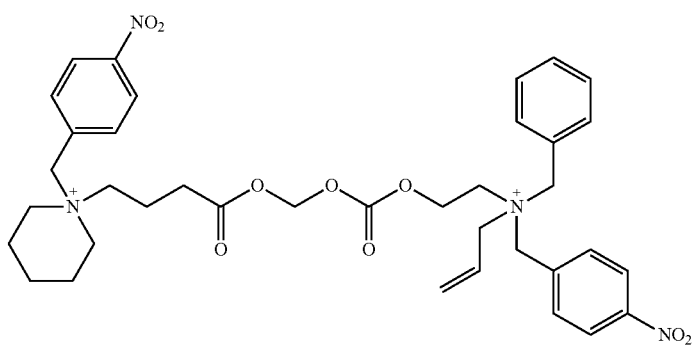 2Br⁻ | 345.1 |
| Compound 45 | 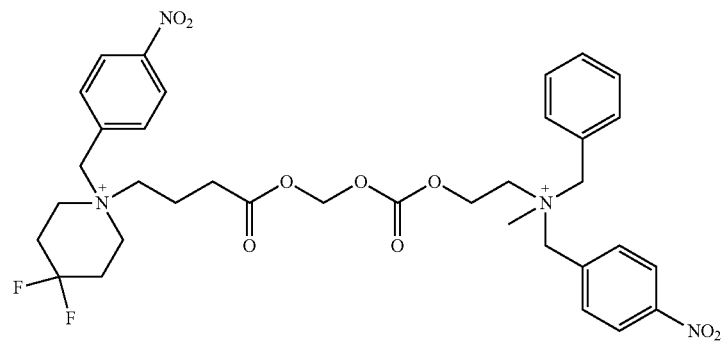 2Br⁻ | 350.1 |
| Compound 46 | 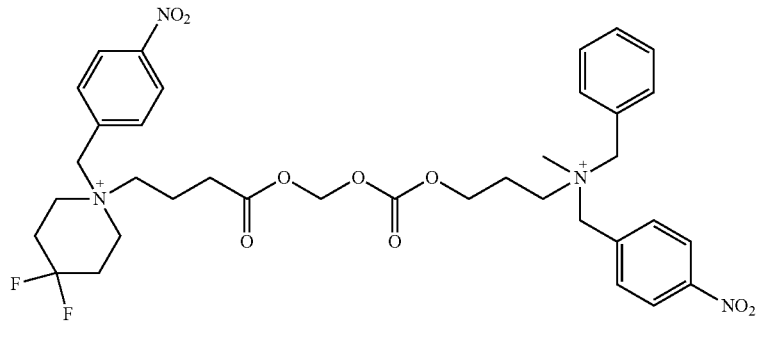 2Br⁻ | 357.1 |

TABLE 1-continued
The structures and mass spectra of part of preferred compounds
| Compound No. | Structure | [M]²⁺ (without anion) |
|---|---|---|
| Compound 47 | 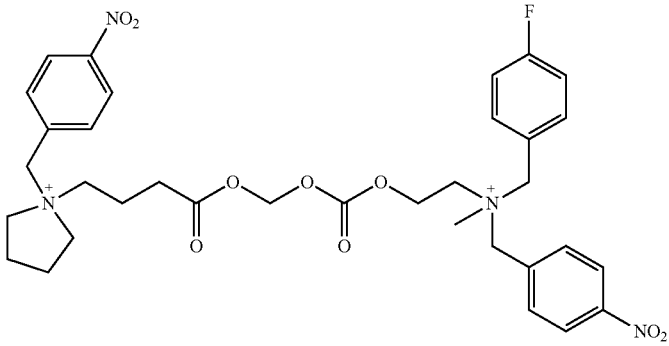 | 334.1 |
| Compound 48 | 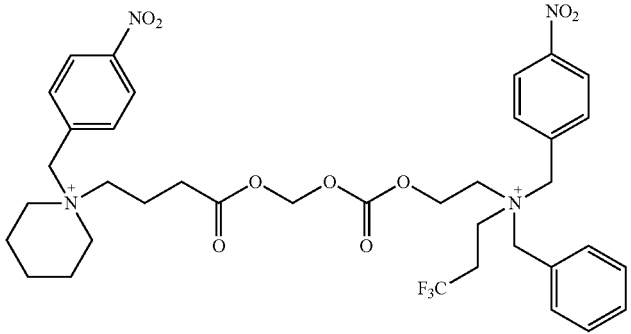 | 373.1 |
| Compound 49 | 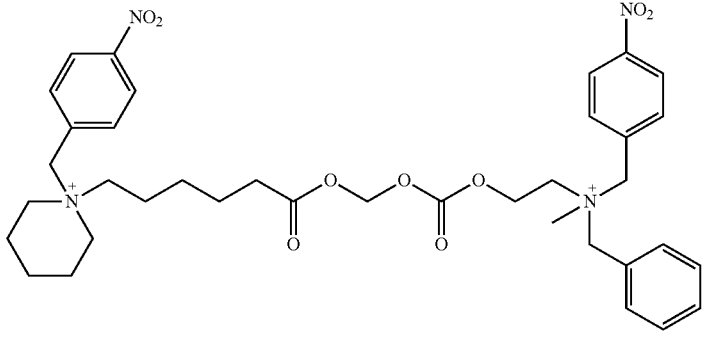 | 346.1 |

TABLE 1-continued

The structures and mass spectra of part of preferred compounds

| Compound No. | Structure | $[M]^{2+}$ (without anion) |
|---|---|---|
| Compound 50 | 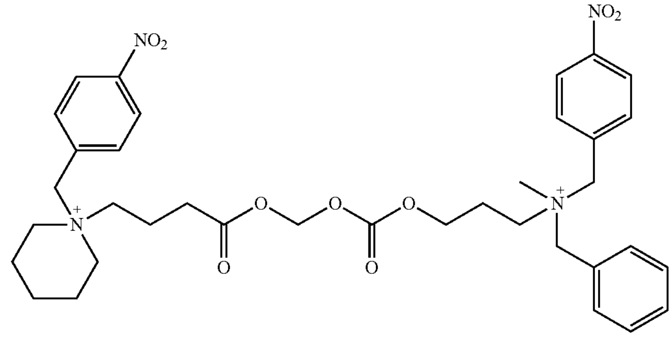 | 339.1 |
| Compound 51 | 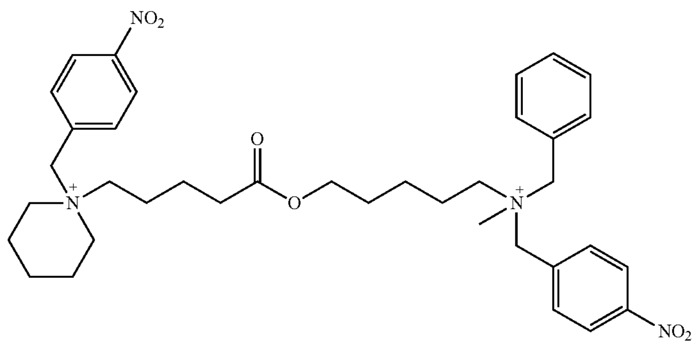 | 323.1 |
| Compound 52 | 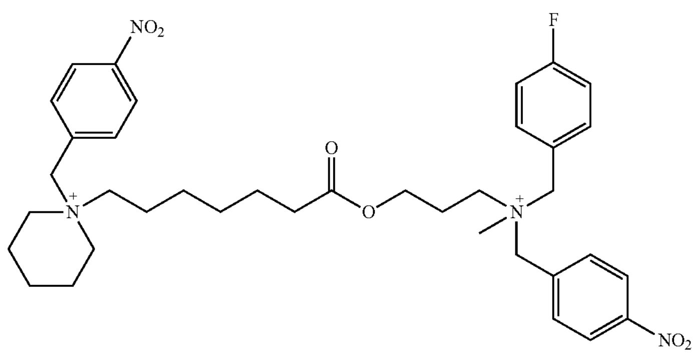 | 332.1 |

The beneficial effect of the present invention was illustrated by the following experimental example.

Experimental Example 1 Experiment on Muscle Relaxation

Male New Zealand white rabbits weighing 2-3.5 kg were used as experimental animals for muscle relaxation test. The specific procedures were: propofol emulsion was intravenously administrated to induce and maintain general anesthesia (induction dose: 10 mg/kg; maintenance dose: 105 mg/hr/kg). Tracheal intubation was carried out and respiratory support was used. After 2× $ED_{95}$ equivalent dose of the positive control drug and the compounds described in the present patent were intravenously injected, the onset time (TOF=0) of the drug and the recovery time (TOF=90%) of muscle relaxation were observed with a neuromuscular transmission monitors (TOF). The results are shown in Table 1.

TABLE 1

The onset time and the duration of muscle relaxant action of drugs in rabbits (N = 8)

| Drug | 2 × $ED_{95}$ (mg/kg) | Onset time (s) | Recovery time (min) |
|---|---|---|---|
| Cisatracurium | 0.08 | >90 | 17.6 ± 5.2 |
| Succinylcholine | 1.8 | <40 | 13.3 ± 3.5 |
| Compound 1 | 0.8 | <40 | 5.2 ± 1.1 |
| Compound 2 | 0.9 | <40 | 6.4 ± 1.4 |
| Compound 3 | 1.8 | <40 | 4.8 ± 0.5 |
| Compound 4 | 1.4 | <40 | 5.4 ± 0.9 |
| Compound 5 | 1.6 | <40 | 5.2 ± 1.2 |
| Compound 6 | 0.8 | <40 | 4.1 ± 1.1 |
| Compound 7 | 1.6 | <40 | 5.2 ± 1.1 |
| Compound 8 | 1.7 | <40 | 7.2 ± 1.4 |
| Compound 9 | 1.6 | <40 | 5.2 ± 1.2 |
| Compound 10 | 2.4 | <40 | 6.2 ± 0.9 |
| Compound 11 | 1.5 | <40 | 7.7 ± 1.6 |
| Compound 12 | 4.4 | <40 | 6.3 ± 2.1 |
| Compound 13 | 6.2 | <40 | 6.9 ± 1.7 |
| Compound 14 | 1.0 | <40 | 4.9 ± .09 |
| Compound 15 | 1.2 | <40 | 5.4 ± 1.1 |
| Compound 19 | 0.8 | <40 | 4.1 ± 0.8 |
| Compound 35 | 1.0 | <40 | 7.2 ± 2.3 |
| Compound 38 | 1.2 | <40 | 4.4 ± 1.1 |
| Compound 45 | 0.8 | <40 | 5.1 ± 1.4 |
| Compound 47 | 1.4 | <40 | 3.1 ± 0.7 |

Above results showed that the compound of the present invention could rapidly produce muscle relaxation in animals (<40 seconds), and the continuous time of muscle relaxation was significantly shorter than that of the positive control drug cisatracurium, even shorter than that of the positive control drug succinylcholine. These characteristics showed that the compounds of the present invention had the characteristics of rapid onset and rapid recovery. In addition, after administration of succinylcholine, the levels of TOF 1-4 decreased in the same proportion until disappearance, showing the typical characteristics of depolarized muscle relaxants, while, after the compound of the present invention and cisatracurium were administrated, the TOF 1-4 of the tested animals successively and gradually decreased, rather than in equal proportion. The change characteristics of TOF indicate that the compound in the present invention belongs to a typical non-depolarizing muscle relaxant.

In summary, the present invention provides the bicationic compound of formula (I), or the stereoisomer or the stereoisomer mixture, or the pharmaceutically acceptable salt, or the solvate, or the crystal, as well as the preparative method thereof. The experiments indicate that compared with the positive control drugs cisatracurium and succinylcholine, the compound of the present invention has more significant characteristics of rapid onset and rapid recovery, and belongs to a typical non-depolarizing muscle relaxant, with a good application prospect.

The invention claimed is:

1. The dicationic compound of formula (I) or a stereoisomer thereof:

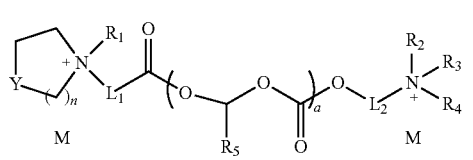

(I)

Wherein, n=1, 2, 3; a=0, 1, 2;

Y is O, substituted or unsubstituted methylene, and the substituted group is halogen and $C_1$-$C_6$ alkyl;

$L_1$ and $L_2$ are independently of each other selected from substituted or unsubstituted $C_1$-$C_8$ alkylene, wherein the substitution means that C in the alkylene is replaced by O or S and/or H is substituted by alkyl or halogen;

$R_1$, $R_2$, $R_3$, and $R_4$ are independently of each other selected from the group consisting of halogen, substituted or unsubstituted and/or saturated or unsaturated $C_1$-$C_{20}$ hydrocarbon groups, in which the substituted groups are selected from one or more halogens, alkoxys, nitros, cyanos, hydroxyls, $C_1$-$C_6$ alkyls, trifluoromethyls, $C_3$-$C_6$ heterocyclic groups, ester groups, alkoxycarbonyl groups, and the skeletons of $R_1$, $R_2$, $R_3$, and $R_4$ contain or don't contain heteroatoms;

$R_5$ is selected from H, $C_1$-$C_6$ alkyl, and $C_3$-$C_6$ cycloalkyl;

M is a pharmaceutically acceptable anion.

2. The dicationic compound of formula (I) or the stereoisomer thereof according to claim 1, characterized in that Y is O, $CH_2$, $CHCH_3$, $CF_2$; said heteroatom is S or O.

3. The dicationic compound of formula (I) or the stereoisomer thereof according to claim 1, characterized in that $L_1$ and $L_2$ are independently of each other selected from substituted or unsubstituted $C_1$-$C_6$ alkylene, wherein the substitution means that C in the alkylene is replaced by O or S and/or H is substituted by $C_1$-$C_3$ alkyl.

4. The dicationic compound of formula (I) or the stereoisomer thereof according to claim 1, characterized in that $R_1$, $R_2$, $R_3$, and $R_4$ are independently of each other selected from the group consisting of halogen, substituted or unsubstituted $C_1$-$C_3$ alkyl, $C_2$-$C_3$ alkenyl,

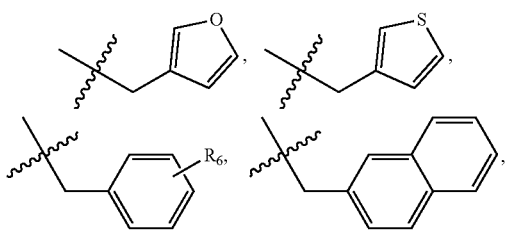

in which $R_6$ is selected from one or more H, nitros, halogens, methoxys, hydroxyls, cyanos, $C_1$-$C_3$ alkyls, phenyls, and trifluoromethyls.

5. The dicationic compound of formula (I) or the stereoisomer thereof according to claim 1, characterized in that n=1, 2; a=0, 1.

6. The dicationic compound of formula (I) or the stereoisomer thereof according to claim 1, characterized in that M is $Br^-$, $Cl^-$, and R—$SO_3^-$, and said R is a hydrocarbon group; preferably, R—$SO_3^-$ is selected from p-toluenesulfonate, methanesulfonate and benzenesulfonate.

7. The dicationic compound of formula (I) or the stereoisomer thereof according to claim 1, characterized in that said halogen is F, Cl, Br, and I.

8. The dicationic compound of formula (I) or the stereoisomer thereof according to claim 1, characterized in that when a=1, said compound is one of the following compounds:

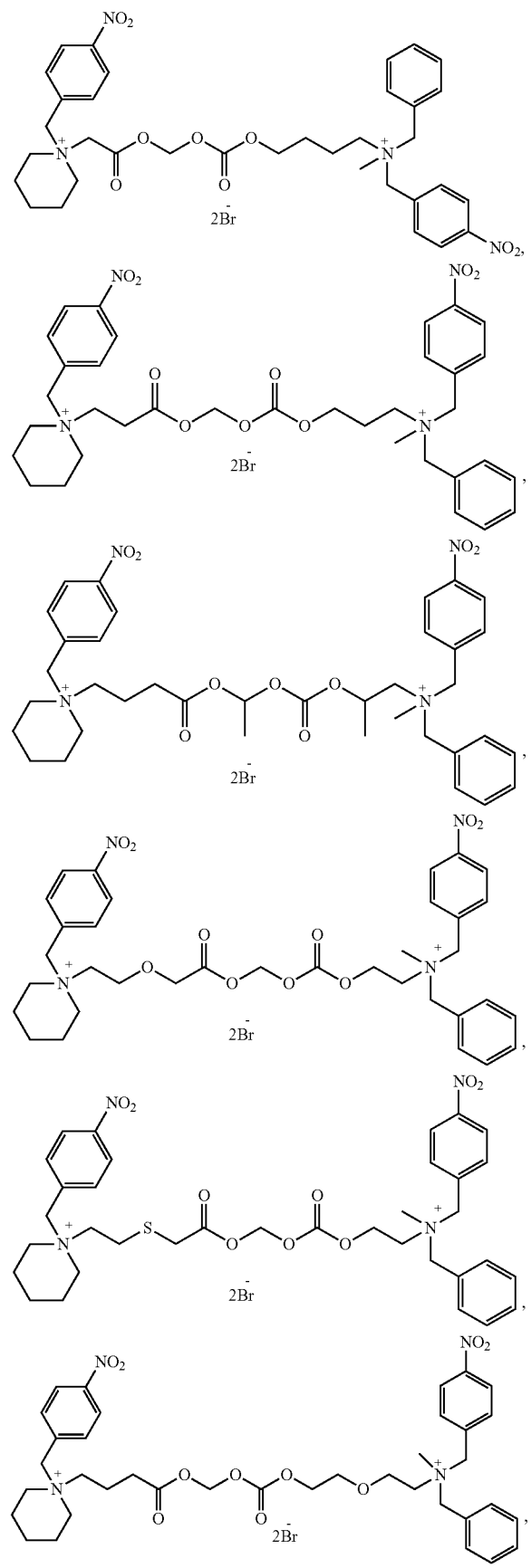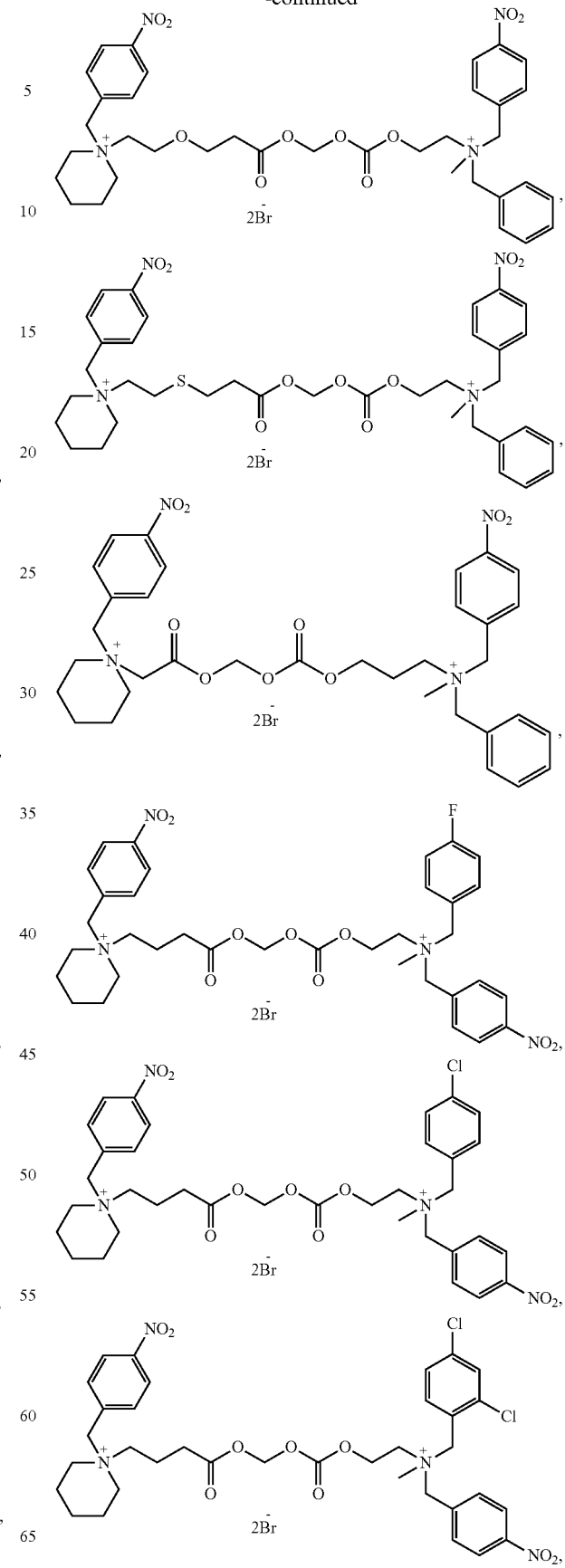

55
-continued
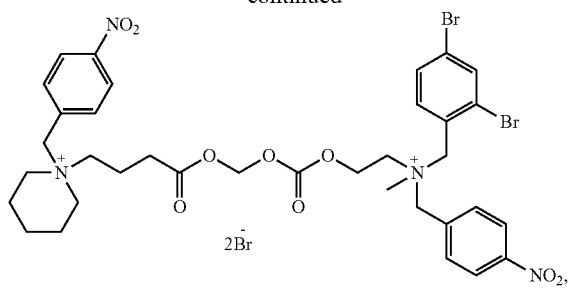
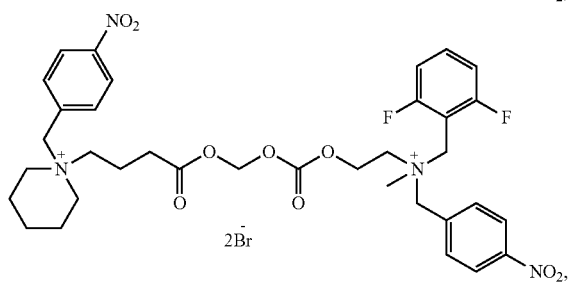
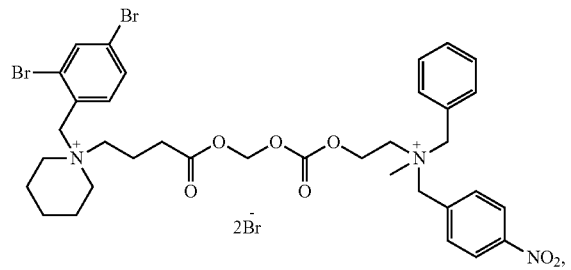
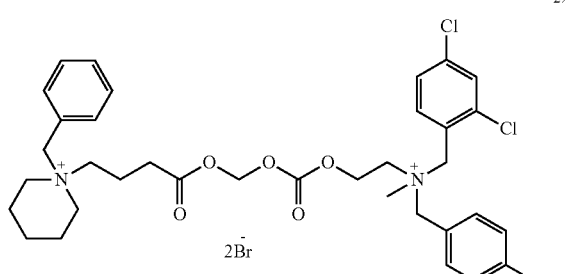
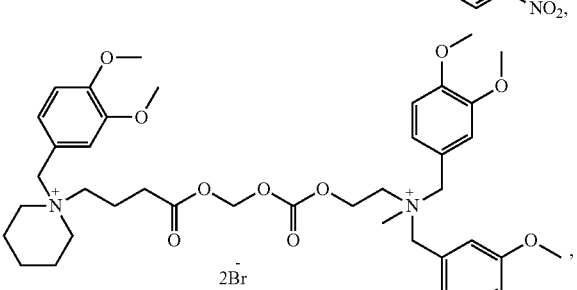
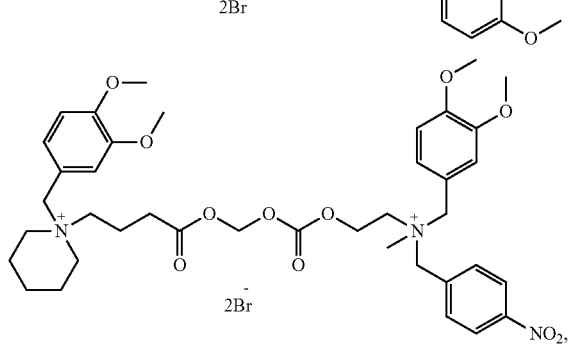
56
-continued
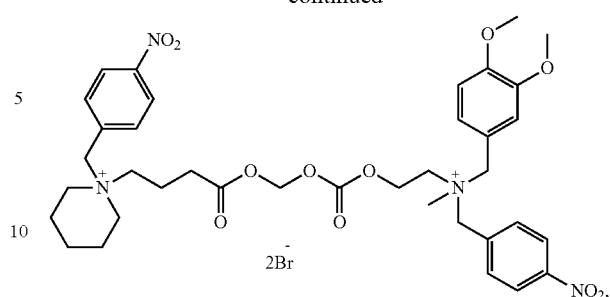
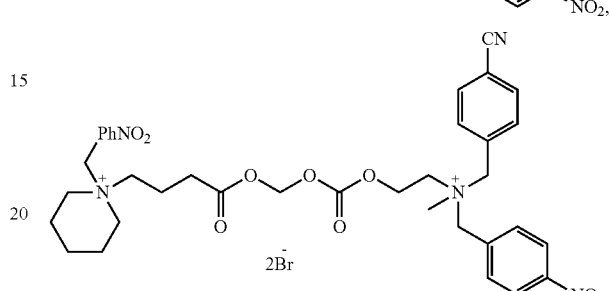
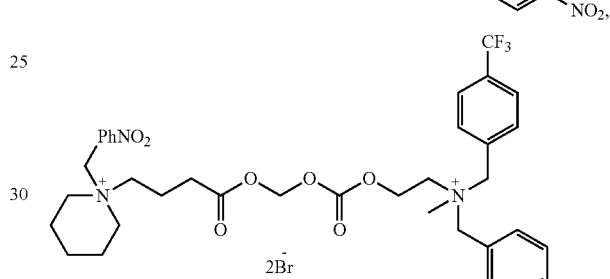
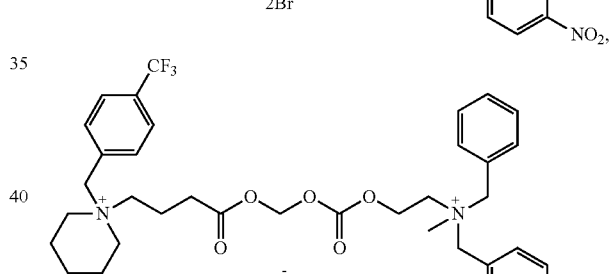
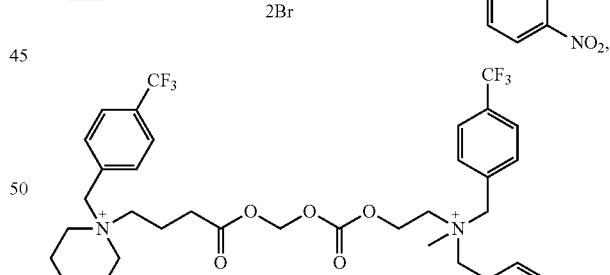
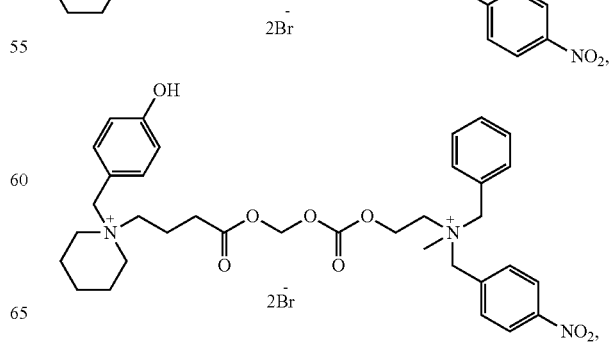

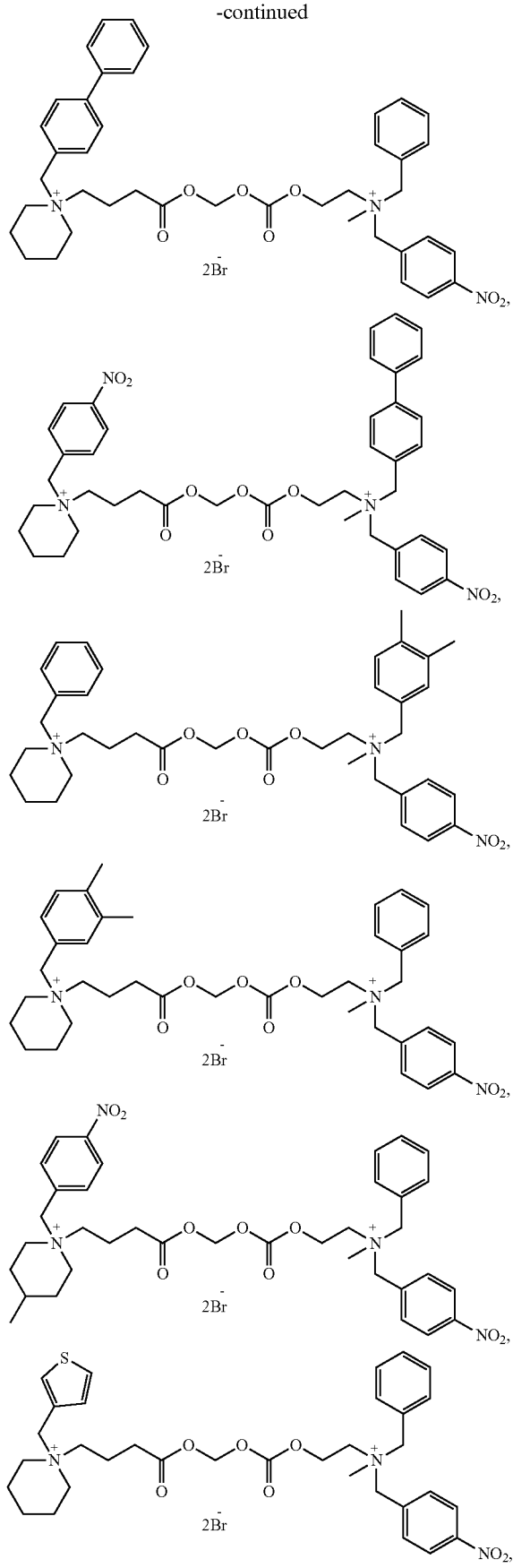
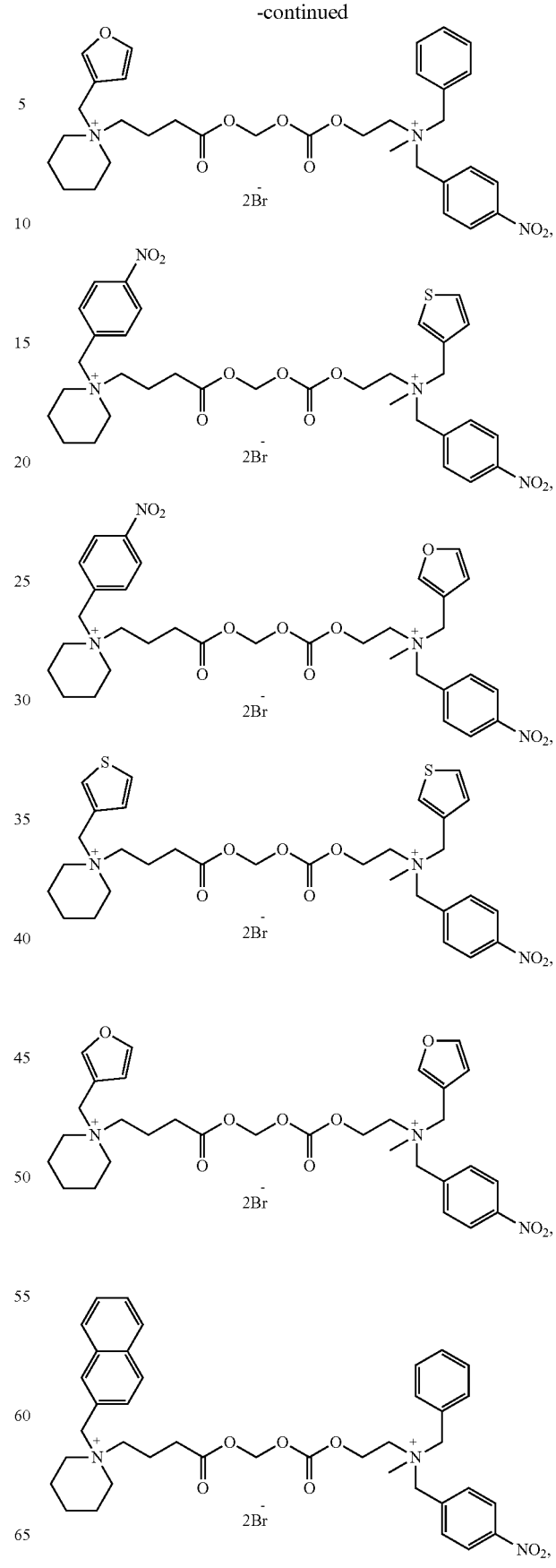

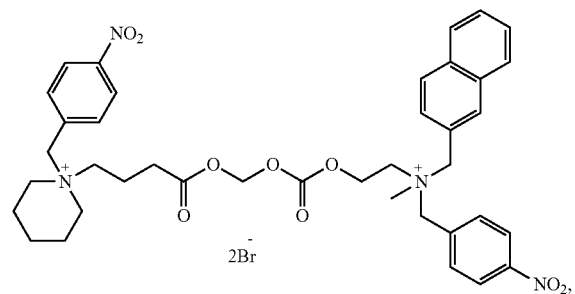
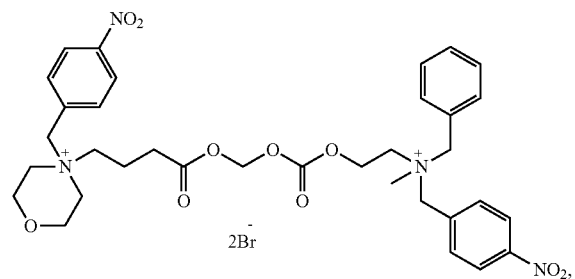
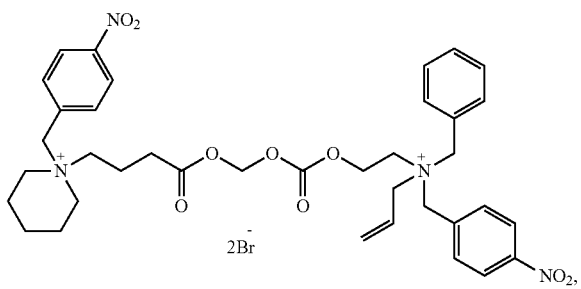
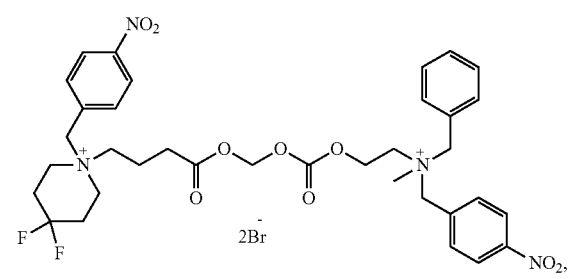
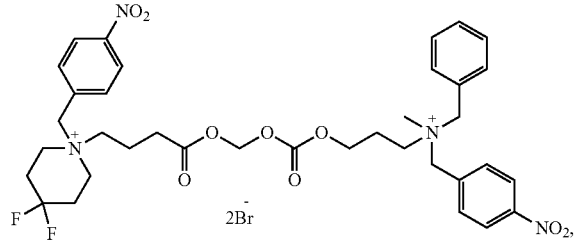
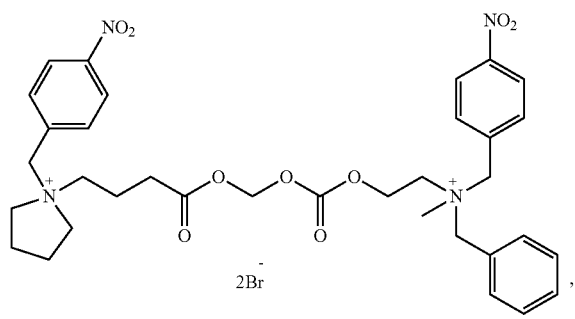
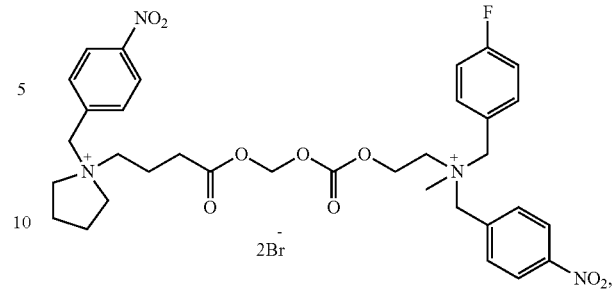
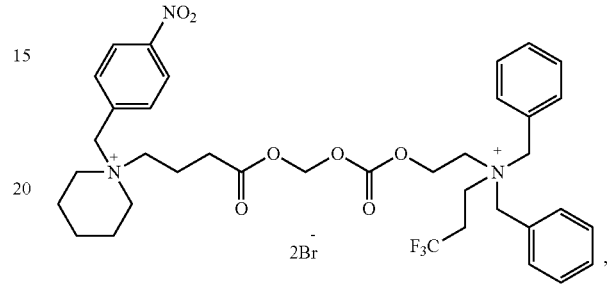
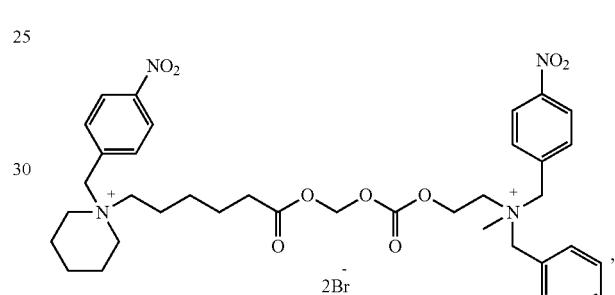
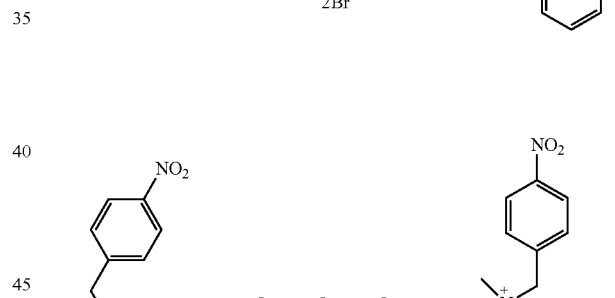
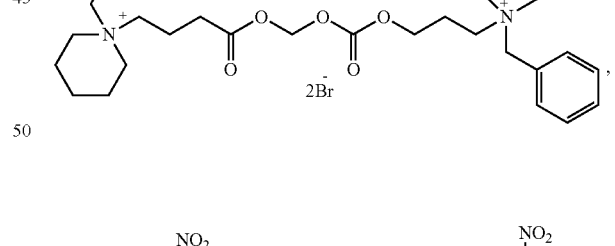
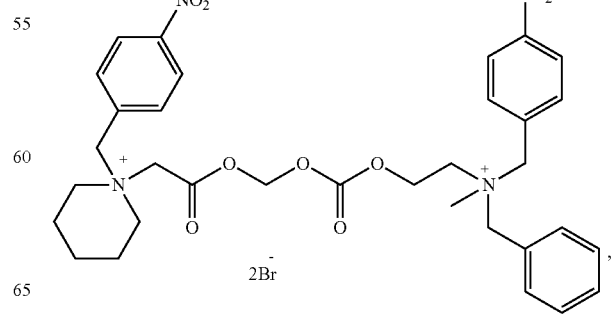

-continued

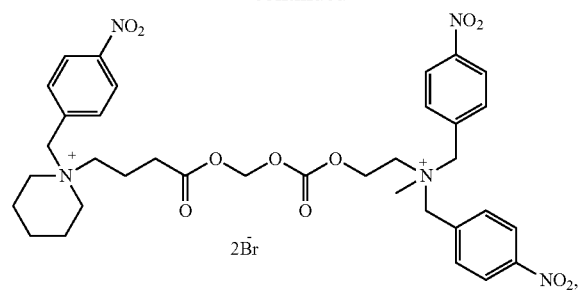

2Br⁻

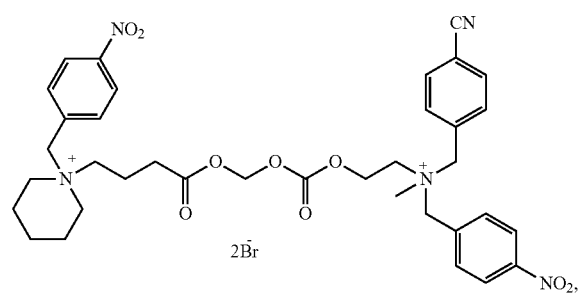

2Br⁻

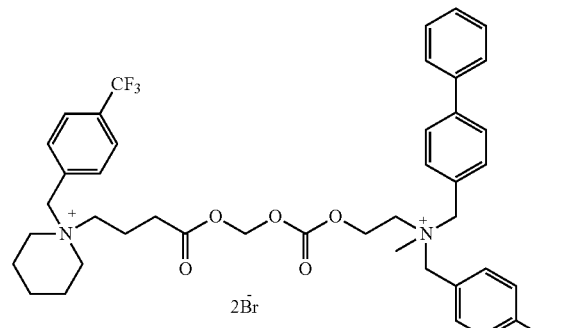

2Br⁻

9. The dicationic compound of formula (I) or the stereoisomer thereof according to claim 1, characterized in that when a=0, said compound is one of the following compounds:

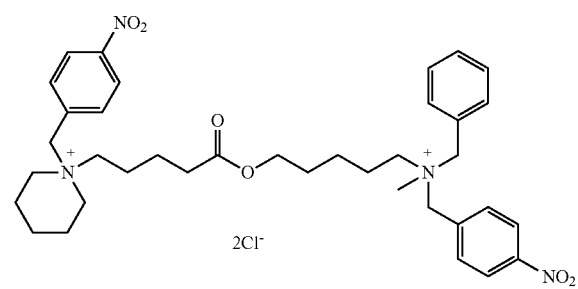

2Cl⁻

-continued
and

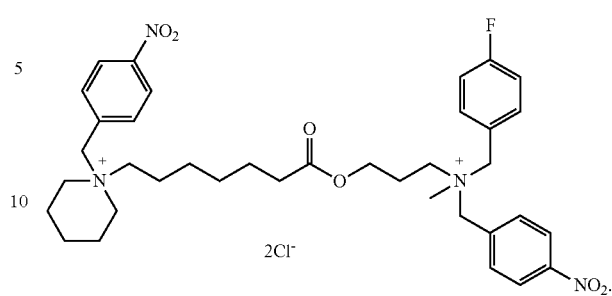

2Cl⁻

10. The preparative method of the dicationic compound of formula (I) or the stereoisomer thereof according to claim 1, characterized in that the method includes the following steps:

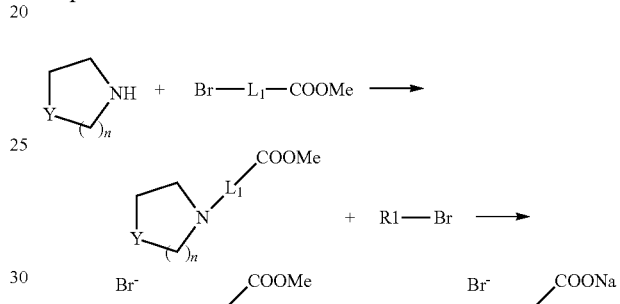

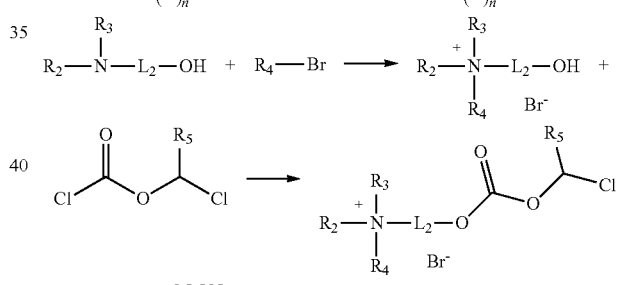

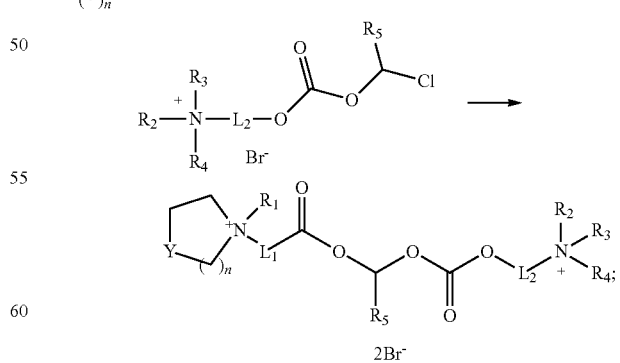

2Br⁻

(1) Preparation of quaternary ammonium intermediate 1

(1-i) Compound a-1 reacts with compound a-2 to prepare compound a-3;

(1-ii) Compound a-3 reacts with compound R₁—Br to prepare compound a-4;

(1-iii) Compound a-4 reacts with sodium hydroxide to prepare quaternary ammonium intermediate 1;

(2) Preparation of quaternary ammonium intermediate 2

(2-i) Compound b-1 reacts with compound R₄—Br to prepare compound b-2;

(2-ii) Compound b-2 reacts with the coupling molecule to prepare quaternary ammonium intermediate 2;

(3) Quaternary ammonium intermediate 1 reacts with quaternary ammonium intermediate 2, to prepare the dicationic compound;

wherein, compound a-1 is

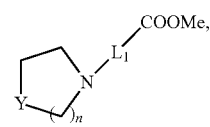

a-1 compound a-2 is

a-2 compound a-3 is

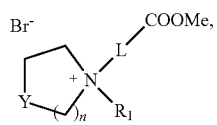

a-3 compound a-4 is

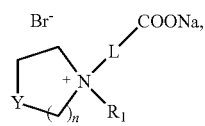

a-4 and quaternary ammonium intermediate 1 is compound b-1 is

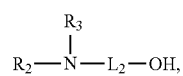

b-1 compound b-2 is

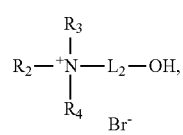

b-2 the coupling molecule is

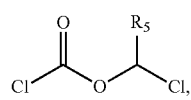

quaternary ammonium intermediate 2 is

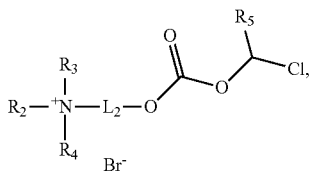

and the dicationic compound is

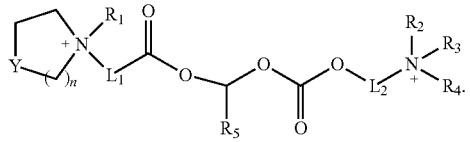

2Br⁻

11. A method for causing muscle relaxation, comprising administering the bicationic compound of formula (I) or the stereoisomer thereof to a subject in need thereof.

12. A muscle relaxant comprising an active ingredient that is the bicationic compound of formula (I) or the stereoisomer thereof according to claim 1 or a pharmaceutically acceptable salt thereof, or a solvate thereof, or a crystalline form thereof, and one or more pharmaceutically acceptable adjuvents.

13. A method for causing muscle relaxation, comprising administering the muscle relaxant of claim 12 to a subject in need thereof.

* * * * *